(12) United States Patent
Shahidi

(10) Patent No.: US 7,844,320 B2
(45) Date of Patent: Nov. 30, 2010

(54) METHOD AND APPARATUS FOR VOLUMETRIC IMAGE NAVIGATION

(76) Inventor: Ramin Shahidi, 1953 Lyon St., San Francisco, CA (US) 94305

( * ) Notice: Subject to any disclaimer, the term of this patent is extended or adjusted under 35 U.S.C. 154(b) by 2319 days.

(21) Appl. No.: 10/229,911

(22) Filed: Aug. 27, 2002

(65) Prior Publication Data

US 2003/0032878 A1 Feb. 13, 2003

Related U.S. Application Data

(63) Continuation of application No. 09/747,463, filed on Dec. 22, 2000, now Pat. No. 6,591,130, which is a continuation of application No. 09/411,363, filed on Sep. 30, 1999, now Pat. No. 6,167,296, which is a continuation of application No. 08/884,289, filed on Jun. 27, 1997, now abandoned.

(60) Provisional application No. 60/020,664, filed on Jun. 28, 1996.

(51) Int. Cl.
A61B 5/05 (2006.01)

(52) U.S. Cl. .................. 600/424; 600/407; 600/426; 600/427; 600/443; 600/445; 606/130

(58) Field of Classification Search .............. 600/410, 600/407, 429, 424, 426, 427, 443, 445; 606/130
See application file for complete search history.

(56) References Cited

U.S. PATENT DOCUMENTS

| | | |
|---|---|---|
| RE30,397 E | 9/1980 | King |
| 4,583,538 A | 4/1986 | Onik et al. |
| 4,770,182 A | 9/1988 | Damadian et al. |
| 4,945,478 A | 7/1990 | Merickel et al. |
| 4,977,505 A | 12/1990 | Pelizzari et al. |
| 5,070,401 A | 12/1991 | Salvati et al. |

(Continued)

OTHER PUBLICATIONS

Supervised Textured Image Segmentation Using Feature Smoothing and Probabilistic Relaxation Techniques, Hsiao et al, Dec. 12, 1989, IEEE Transactions on Pattern Analysis and Mechine Intelligence vol. II No. 12.*

(Continued)

*Primary Examiner*—Brian Casler
*Assistant Examiner*—Joel M Lamprecht
(74) *Attorney, Agent, or Firm*—Alexander Chen, Esq.

(57) ABSTRACT

A surgical navigation system has a computer with a memory and display connected to a surgical instrument or pointer and position tracking system, so that the location and orientation of the pointer are tracked in real time and conveyed to the computer. The computer memory is loaded with data from an MRI, CT, or other volumetric scan of a patient, and this data is utilized to dynamically display 3-dimensional perspective images in real time of the patient's anatomy from the viewpoint of the pointer. The images are segmented and displayed in color to highlight selected anatomical features and to allow the viewer to see beyond obscuring surfaces and structures. The displayed image tracks the movement of the instrument during surgical procedures. The instrument may include an imaging device such as an endoscope or ultrasound transducer, and the system displays also the image for this device from the same viewpoint, and enables the two images to be fused so that a combined image is displayed. The system is adapted for easy and convenient operating room use during surgical procedures.

25 Claims, 17 Drawing Sheets

U.S. PATENT DOCUMENTS

| | | | |
|---|---|---|---|
| 5,078,140 A | 1/1992 | Kwoh | |
| 5,222,499 A | 6/1993 | Allen et al. | |
| 5,230,338 A | 7/1993 | Allen et al. | |
| 5,261,404 A | 11/1993 | Mick et al. | |
| 5,299,253 A | 3/1994 | Wessels | |
| 5,313,306 A | 5/1994 | Kuban et al. | |
| 5,337,732 A | 8/1994 | Grundfest et al. | |
| 5,363,475 A | 11/1994 | Baker et al. | |
| 5,389,101 A | 2/1995 | Heilbrun et al. | |
| 5,417,210 A | 5/1995 | Funda et al. | |
| 5,419,320 A | 5/1995 | Kawaguchi et al. | |
| 5,454,371 A | 10/1995 | Fenster et al. | |
| 5,458,126 A | 10/1995 | Cline et al. | |
| 5,491,510 A | 2/1996 | Gove | |
| 5,531,520 A | 7/1996 | Grimson et al. | |
| 5,540,229 A | 7/1996 | Collet-Billon et al. | |
| 5,546,807 A | 8/1996 | Oxaal et al. | |
| 5,562,095 A | 10/1996 | Downey et al. | |
| 5,572,999 A | 11/1996 | Funda et al. | |
| 5,585,813 A | 12/1996 | Howard | |
| 5,604,848 A | 2/1997 | Harada et al. | |
| 5,608,849 A | 3/1997 | King, Jr. | |
| 5,611,025 A | 3/1997 | Lorensen et al. | |
| 5,622,170 A | 4/1997 | Schulz | |
| 5,671,381 A | 9/1997 | Strasnick et al. | |
| 5,682,886 A | 11/1997 | Delp et al. | |
| 5,694,945 A * | 12/1997 | Ben-Haim | 600/407 |
| 5,704,897 A | 1/1998 | Truppe | |
| 5,740,802 A | 4/1998 | Nafis et al. | |
| 5,772,594 A | 6/1998 | Barrick | |
| 5,776,050 A | 7/1998 | Chen et al. | |
| 5,781,195 A | 7/1998 | Marvin | |
| 5,797,849 A | 8/1998 | Vesely et al. | |
| 5,800,352 A | 9/1998 | Ferre et al. | |
| 5,815,126 A | 9/1998 | Fan et al. | |
| 5,833,608 A | 11/1998 | Acker | |
| 5,833,627 A | 11/1998 | Shmulewitz et al. | |
| 5,836,954 A | 11/1998 | Heilbrun et al. | |
| 5,842,473 A | 12/1998 | Fenster et al. | |
| 5,855,553 A | 1/1999 | Tajima et al. | |
| 5,868,673 A | 2/1999 | Vesely | |
| 5,871,018 A | 2/1999 | Delp et al. | |
| 5,882,206 A | 3/1999 | Gillio | |
| 5,887,121 A | 3/1999 | Funda et al. | |
| 5,891,034 A | 4/1999 | Bucholz | |
| 5,892,538 A | 4/1999 | Gibas | |
| 6,006,126 A * | 12/1999 | Cosman | 600/426 |

OTHER PUBLICATIONS

Anon J.B., et al., "Computer-Assisted Endoscopic Sinus Surgery—Current Experience and Future Developments" Operative Techniques in Otolaryngology (1995) 6(3):163-170.

Ault, T. and Siegel, M.W., "Frameless Patient Registration Using Ultrasonic Imaging: A Preliminary Study" J. Image Guid. Surg. (1995) 1:94-102.

Bainville, E., et al., "Computer Generated Visual Assistance During Retroperitoneoscopy" Comput. Biol. Med. (1995) 25(2):165-171.

Brady, M.L., et al., "Interactive Navigation Inside 3D Radiological Images" IEEE (1995) pp. 33-40.

Brett, P.N., et al., "Automatic Surgical Tools for Penetrating Flexible Tissues" IEEE Engin. in Med. and Biol. May/Jun. 1995:264-270.

Burckhardt, C.W., et al., "Stereotactic Brain Surgery" IEEE Engin. in Med. and Biol. May/Jun. 1995:314-317.

Chang, Y-K., et al., "Visualizing the Anatomical-Functional Correlation of the Human Brain" SPIE (1995) 2410:32-41.

Charles, S., "Dexterity Enhancement for Surgery" MRCAS (1994) pp. 145-160.

Chinzei, K., et al., "Quantitative Integration of Multimodality Medical Images" SPIE (1992) 1808:187-195.

Cinquin, P., et al., "Computer Assisted Medical Interventions" IEEE Engin. in Med. and Biol. May/Jun. 1995:254-263.

Cohen, D.S., et al., "Effects of coregistration of MR to CT images on MR stereotactic accuracy" J. Neurosurg. (1995) 82:772-779.

Colchester, A.C.F, et al., "Craniotomy Simulation and Guidance Using a Stereo Video Based Tracking System (VISLAN)" SPIE (1994) 2359:541-551.

Collins, D.L., et al., "An Automated 3D non-linear image deformation procedure for Determination of Gross Morphometric Variability in Human Brain" SPIE (1994) 2359:180-190.

Davey, B.L.K., et al., "Multimodality Interactive Stereoscopic Image-Guided Neurosurgury" SPIE (1994) 2359:526-536.

Ehricke, H-H., et al., "Interactive 3D-graphics workstations in stereotaxy: Clinical requirements, algorithms and solutions" SPIE (1992) 1808:548-558.

Finlay, P.A., and Ornstein, M.H., "Controlling the Movement of a Surgical Laparoscope" IEEE Engin. in Med. and Biol. May/Jun. 1995:289-291.

Gee, J.C., et al., "Matching Structural Images of the Human Brain Using Statistical and Geometrical Image Features" SPIE (1994) 2359:191-204.

Giorgi, C., et al., "Robot-Assisted Microscope for Neurosurgery" J. Image Guid. Surg. (1995) 1:158-163.

Goble J.C., et al., "A Real-Time System for 3D Neurosurgical Planning" SPIE (1994) 2359:552-563.

Grimson, E., et al., "Automated Registration for Enhanced Reality Visualization in Surgery" AAAL Spring Symposium (1994) pp. 26-29.

Hamadeh, A., et al., "Anatomy Based Multi-modal Medical Image Registration for Computer Integrated Surgery" SPIE (1994) 2355:178-188.

Henri, C.J., et al., "Towards Frameless Stereotaxy: Anatomical-Vascular Correlation and Registration" SPIE (1992) 1808:214-224.

Hill, D.L.G., et al., "Visualisation of multi-modal images for the planning of skull base surgery" SPIE (1992) 1808:564-573.

Hill, D.L.G., et al., "Voxel Similarity Measures for Automated Image Registration" SPIE (1994) 2359:205-216.

Horstmann, G.A., et al., " Micro-Stereometry: A Frameless Computerized Navigating System for Open Microsurgery".Comput. Med. Imaging and Graphics (1994) 18(4):229-233.

Jiang, H., et al., "A New Approach to 3-D Registration of Multimodality Medical Images by Surface Matching" SPIE (1992) 1808:196-213.

Kazanzides, P., et al., "An Integrated System for Cementless Hip Replacement" IEEE Engin. in Med. and Biol. May/Jun. 1995:307-313.

Kienzle III, T.C., et al., "Total Knee Replacement" IEEE Engin. in Med. and Biol. May/Jun. 1995:301-306.

Kikinis, R., et al., "Interactive visualization and manipulation of 3D reconstructions for the planning of surgical procedures" SPIE (1992) 1808:559-563.

Kikinis, R., et al., "Image guidance techniques for neurosurgery" SPIE (1994) 2359:537-540.

Lea, J.T., et al., "Diagramming Registration Connectivity and Structure" IEEE Engin. in Med. and Biol. May/Jun. 1995:271-278.

Liu, A., et al., "Volume registration using the 3D core" SPIE (1994) 2359:217-226.

Matz, P., et al., "Cavernous Malformations: Results of Image-Guided Resection" J. Image Guid. Surg. (1995) 1:273-279.

Merloz et al., "Pedicle Screw Placement Using Image Guided Techniques" Clin. Orthop. (1998) 354:39-48.

Morita, A. and Kelly, P.J., "Resection of Intraventricular Tumors via a Computer-assisted Volumetric Stereotactic Approach" Neurosurgery (1993) 32(6):920-927.

Nolte, L., et al., "A Novel Approach to Image Guided Spine Surgery" SPIE (1994) 2359:564-573.

Peifer, J.W., et al., "3-D registration and visualization of reconstructed coronary arterial trees on myocardial perfusion distributions" SPIE (1992) 1808:225-234.

Pérault, C., et al., "Automatic superimposition of CT and SPET immunoscintigraphic images in the pelvis" SPIE (1992) 1808:235-240.

Sclabassi, R.J., et al., "NeuroNet: Collaborative Intraoperative Guidance and Control" IEEE Computer Graphics and Applications (1996) pp. 39-45.

Simon, D.A., et al., "Techniques for Fast and Accurate Intrasurgical Registration" J. Image Guid. Surg. (1995) 1:17-29.

Taneja, U., et al., "Evaluating the accuracy of three-dimensional image registration algorithms used in multimodal image fusion" SPIE (1994) 2359:238-250.

Taylor, R.H., et al., "A Telerobotic Assistant for Laparoscopic Surgery" IEEE Engin. in Med. and Biol. May/Jun. 1995:279-288.

Tebo, S.A., et al., "An Optical 3D Digitizer for Frameless Stereotactic Surgery" IEEE Computer Graphics and App. Jan. 1996:55-63.

van den Elsen, P.A., et al., Image Fusion using geometrical features SPIE (1992) 1808:172-186.

van den Elsen, P.A., et al., "Medical Image Matching—A Review with Classification" IEEE Engin. in Med. and Biol. Mar. 1993:26-39.

van den Elsen, P.A., et al., "Grey value correlation techniques used for automatic matching of CT and MR brain and spine images" SPIE (1994) 2359:227-237.

Wells III, W.M., et al., "Multi-modal volume registration by maximization of mutual information" Med. Image Analysis (1996) 1(1):35-51.

Zamorano, L., et al., "Computer-Assisted Neurosurgery System: Wayne State University Hardware and Software Configuration" Comput. Med. Imaging and Graphics (1994) 18(4):257-271.

Zhuang, H., et al., "Practical Fusion Algorithms for Rotation Matrices: A Comparative Study" J. of Robotic Sys. (1992) 9(7):915-931.

* cited by examiner

METHOD AND APPARATUS FOR VOLUMETRIC IMAGE NAVIGATION

CROSS REFERENCE TO RELATED APPLICATIONS

This application is a continuation application of U.S. Pat. application Ser. No. 09/747,463 filed Dec. 22, 2000 now U.S. Pat. No. 6,591,130, which is a continuation of U.S. patent application Ser. No. 09/411,363 filed Sep. 30, 1999 now U.S. Pat. No. 6,167,296, issued Dec. 26, 2000, which is a continuation of U.S. patent application Ser. No. 08/884,289, filed Jun. 27, 1997, now abandoned, which claims the benefit of U.S. Provisional Application No. 60/020,664, filed Jun. 28, 1996; all of which are incorporated in their entirety herein by reference.

BACKGROUND OF THE INVENTION

1. Field of the Invention

This invention pertains generally to systems and methods for generating images of three dimensional objects for navigation purposes, and more particularly to systems and methods for generating such images in medical and surgical applications.

2. Description of the Background Art

Precise imaging of portions of the anatomy is an increasingly important technique in the medical and surgical fields. In order to lessen the trauma to a patient caused by invasive surgery, techniques have been developed for performing surgical procedures within the body through small incisions with minimal invasion. These procedures generally require the surgeon to operate on portions of the anatomy that are not directly visible, or can be seen only with difficulty. Furthermore, some parts of the body contain extremely complex or small structures and it is necessary to enhance the visibility of these structures to enable the surgeon to perform more delicate procedures. In addition, planning such procedures requires the evaluation of the location and orientation of these structures within the body in order to determine the optimal surgical trajectory.

New diagnostic techniques have been developed in recent years to obtain images of internal anatomical structures. These techniques offer great advantages in comparison with the traditional X-ray methods. Newer techniques include microimpulse radar (MIR), computer tomography (CT) scans, magnetic resonance imaging (MRI), positron emission tomography (PET), ultrasound (US) scans, and a variety of other techniques. Each of these methods has advantages and drawbacks in comparison with other techniques. For example, the MRI technique is useful for generating three-dimensional images, but it is only practical for certain types of tissue, while CT scans are useful for generating images of other anatomical structures. Ultrasound scanning, in contrast, is a relatively rapid procedure; however it is limited in its accuracy and signal-to-noise ratio.

The imaging problem is especially acute in the field of neurosurgery, which involves performing delicate surgical procedures inside the skull of the patient. The above techniques have improved the surgeon's ability to locate precisely various anatomical features from images of structures within the skull. However this has only limited usefulness in the operating room setting, since it is necessary to match what the surgeon sees on the 2D image with the actual 3D patient on the operating table. The neurosurgeon is still compelled to rely to a considerable extent on his or her knowledge of human anatomy.

The stereotactic technique was developed many years ago to address this problem. In stereotactic surgery, a frame of reference is attached to the patient's head which provides reference points for the diagnostic images. The device further includes guides for channeling the surgical tool along a desired trajectory to the target lesion within the brain. This method is cumbersome and has the drawback that the surgeon cannot actually see the structures through which the trajectory is passing. There is always the risk of damage to obstacles in the path of the incision, such as portions of the vascular or ventricular system. In essence, with previous neurosurgical techniques the surgeon is in the position much like that of a captain piloting a vessel traveling in heavy fog through waters that have many hazards, such as shoals, reefs, outcroppings of rocks, icebergs, etc. Even though the captain may have a very good map of these hazards, nevertheless there is the constant problem of keeping track of the precise location of the vessel on the map. In the same way, the neurosurgeon having an accurate image scan showing the structures within the brain must still be able to precisely locate where the actual surgical trajectory lies on the image in order to navigate successfully to the target location. In the operating room setting, it is further necessary that this correlation can be carried out without interfering with the numerous other activities that must be performed by the surgeon.

The navigation problem has been addressed in U.S. Pat. No. 5,383,454, issued Jan. 24, 1995 (Bucholz). This patent describes a system for indicating the position of a surgical probe within a head on an image of the head. The system utilizes a stereotactic frame to provide reference points, and to provide means for measuring the position of the probe tip relative to these reference points. This information is converted into an image by means of a computer.

U.S. Pat. No. 5,230,623, issued Jul. 27, 1993 (Guthrie), discloses an operating pointer whose position can be detected and read out on a computer and associated graphics display. The pointer can also be used as a "3D mouse" to enable the surgeon to control the operation of the computer without releasing the pointer.

U.S. Pat. No. 5,617,857, issued Apr. 8, 1997 (Chader et al.) sets forth an imaging system and method for interactively tracking the position of a medical instrument by means of a position-detecting system. The pointer includes small light-emitting diodes (LED), and a stationary array of radiation sensors is provided for detecting pulses emitted by these LED's and utilizing this information to ascertain dynamically the position of the pointer. Reference is made also to U.S. Pat. No. 5,622,170, issued Apr. 22, 1997 (Schulz), which describes a similar system connected to a computer display for displaying the position of an invasive surgical probe relative to a model image of the object being probed (such as a brain).

U.S. Pat. No. 5,531,227, issued Jul. 2, 1996 (Schneider) explicitly addresses the problem recognized in many other references that it is desirable to provide a real time display of a surgical probe as it navigates through the brain. This patent describes a system for providing images along the line of sight of the surgeon in a dynamic real-time fashion. In this system the images that are displayed are resliced images from a three-dimensional-data reconstruction which are sections or slices orthogonal to the line of sight, taken at various positions along this line specified by the user. Thus, while the viewpoint for the line of sight is always external to the body, the sectional planes that are used to define the virtual images may constitute various slices through the body chosen by the surgeon. These images may be superimposed on actual images obtained by an image recording device directed along the line of sight such as a video camera attached to the surgeon's head, and the composite images may be displayed.

The systems described above attempt to address the navigation problem in various ways, and they all have the common drawback of requiring a certain level of abstract visualization by the surgeon during an operating room procedure. When the surgeon is proceeding through the brain toward a target tumor or lesion, it is desirable to be fully aware of all of the structures around the surgical trajectory. With previous systems the displays that are presented do not provide all of this information in a single convenient real-time display, and they require the viewer to piece together and re-orient the displayed information to obtain a mental picture of the surrounding structures. These are serious practical disadvantages in an operating room setting. What is absent from previous systems is a 3D display that shows, in a real-time view, the various structures looking ahead from the surgical probe along a line of sight into the brain in three and two dimensions, including structures hidden by other features.

SUMMARY OF THE INVENTION

The present invention provides an improved system and method for displaying 3D images of anatomical structures in real time during surgery to enable the surgeon to navigate through these structures during the performance of surgical procedures. This system is also useful in planning of surgical procedures. The system includes a computer with a display and input devices such as a keyboard and mouse. The system also includes a position tracking system that is connected both to the computer and also to the surgical probes or other instruments that are used by the surgeon. The position tracking system provides continual real time data to the computer indicating the location and orientation of the surgical instrument in use. The computer further includes a memory containing patient data produced by imaging scans, such as CT or MRI scans, from which 2-dimensional and 3-dimensional images of the anatomical structure may be generated. Means are provided for registration of these images with respect to the patient.

The computer memory is further provided with programs that control the generation of these anatomical images. These programs include software for segmentation of the scan images to identify various types of structures and tissues, as well as the reconstruction of 2D and 3D images from the scan data. This software allows these images to be displayed with various magnifications and orientations, and with various sectional views produced by slice planes in various locations and orientations, all controlled by the surgeon.

This image-generating software has the important feature that it produces 3D images that are perspective views of the anatomical structures, with user-controlled means for varying the viewing orientation and location, and also varying the displayed transparency or opacity of various types of tissues, structures, and surfaces in the viewed region of interest. This enables the user to effectively "see through" surfaces and structures in the line of sight of the image to reveal other structures that would otherwise be hidden in that particular view.

Further, the images are generated from the viewpoint of the surgical probe or instrument that is in use, looking from the tip of the instrument along its longitudinal axis. Thus, when an invasive surgical instrument such as a scalpel or forceps is inserted into an incision in the body, the display provides a three dimensional perspective view of anatomical structures from a viewpoint inside the body. These images are all generated in real time "on the fly". Thus, as the instrument is moved or rotated, the position tracking system continually provides data to the computer indicating the location and orientation of the instrument, and the displayed image is continually updated to show the structures toward which the instrument is pointing.

In addition, for probes or instruments being used that are capable themselves of generating images, such as ultrasound probes, endoscopes, or surgical microscopes, the system provides means for integrating these images with those generated from the scan data. The software enables the user to overlay the "actual images" generated by these instruments with the "virtual images" generated from the scan data.

It is an object of this invention to provide a system and method for generating an image in three dimensional perspective of anatomical structures encountered by a surgeon during the performance of surgical procedures.

A second object of this invention is to provide a system and method for generating such an image with user-controlled means for varying the location and orientation of the viewpoint corresponding to the image.

Another object of this invention is to provide a system and method for generating such an image with user-controlled means for varying the opacity of structures and surfaces in the viewed region of interest, so that the displayed image shows structures and features that would be otherwise hidden in a normal view.

Yet another object of this invention is to provide a system and method for generating such an image with a viewpoint located at the tip of the instrument being used by the surgeon in the direction along the longitudinal axis of the instrument.

Still another object of this invention is to provide a system and method for generating such an image in real time, such that the displayed image continually corresponds to the position of the instrument being used by the surgeon.

Yet a further object of this invention is to provide a system and method for comparing and combining such an image with the image produced by an image-generating instrument being used by the surgeon.

These and other objects, advantages, characteristics and features of the invention may be better understood by examining the following drawings together with the detailed description of the preferred embodiments.

DETAILED DESCRIPTION OF THE PREFERRED EMBODIMENTS

Figure 1:
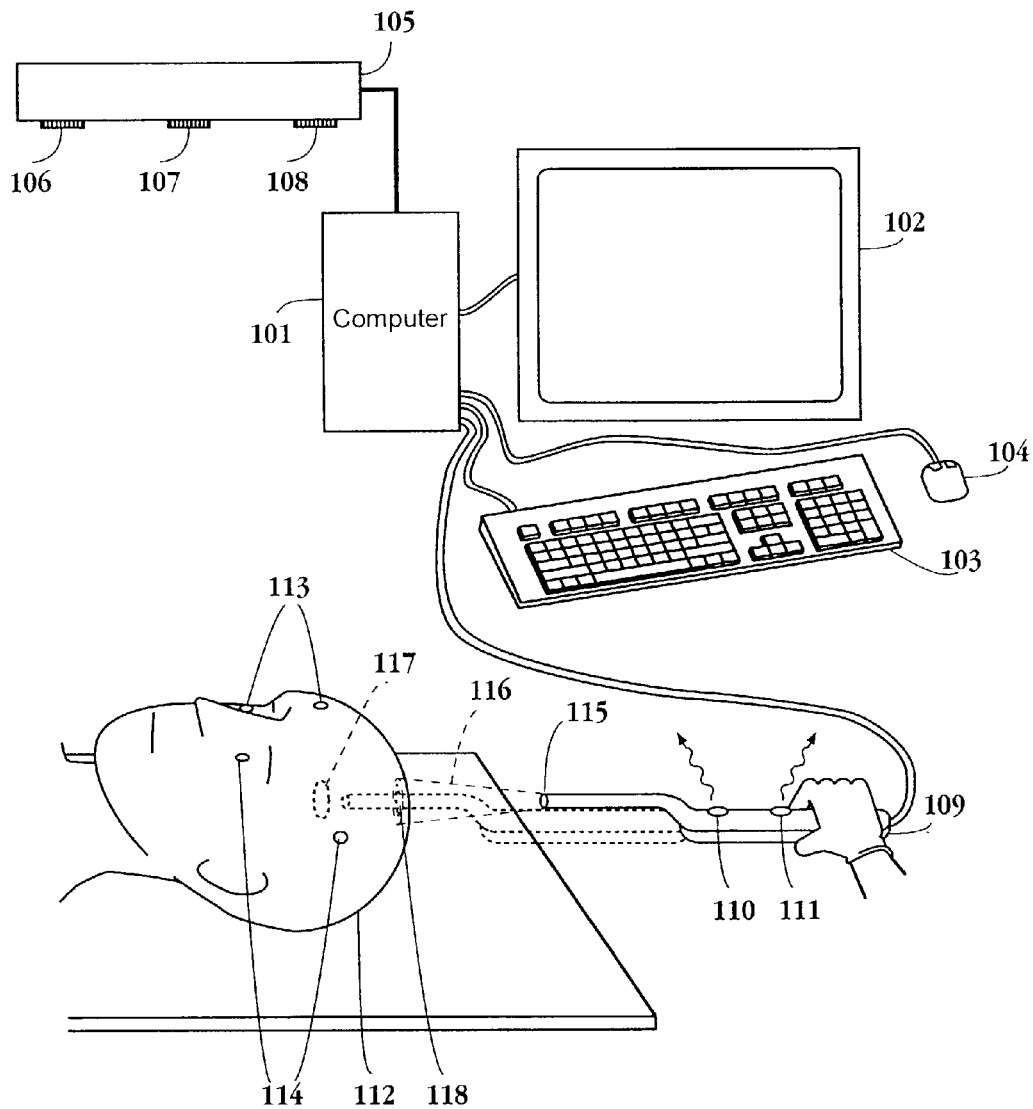
FIG. 1 is a schematic perspective drawing of the apparatus of the present invention in operating room use during the performance of neurosurgical procedures.

FIG. 1 shows the apparatus of the invention as used in performing or planning a neurosurgery operation. In this drawing the patient's head 112, has a tumor or lesion 117, which is the target object of the operation. Fiducial markers 113, 114 are attached to the head to enable registration of images generated by previously obtained scan data according to techniques familiar to persons of ordinary skill in the relevant art. A surgical probe or instrument 109 held by the surgeon is directed toward the tissues of interest. A computer 101 is connected to user input devices including a keyboard 103 and mouse 104, and a video display device 102 which is preferably a color monitor. The display device 102 is located such that it can be easily viewed by the surgeon during an operation, and the user input devices 103 and 104 are placed within easy reach to facilitate use during the surgery. The apparatus further includes a position tracking system, which is preferably an optical tracking system (hereafter "OTS") having a sensing unit 105 mounted overhead in view of the operating table scene, and at least two light emitting diodes (LED's) 110, 111 mounted on the surgical instrument 109. These LED's preferably emit continuous streams of pulsed infrared signals which are sensed by a plurality of infrared sensors 106, 107, 108 mounted in the sensing unit 105 in view of the surgical instrument 109. The instrument 109 and the sensing unit 105 are both connected to the computer 101, which controls the timing and synchronization of the pulse emissions by the LED's and the recording and processing of the infrared signals received by the sensors 106-108. The OTS further includes software for processing these signals to generate data indicating the location and orientation of the instrument 109. The OTS generates the position detecting data on a real time continuous basis, so that as the surgical instrument 109 is moved, its position and orientation are continually tracked and recorded by the sensing unit 105 in the computer 101. The OTS may be preferably of the type known as the "FlashPoint 3-D Optical Localizer", which is commercially available from Image Guided Technologies of Boulder, Colo., similar to the systems described in U.S. Pat. Nos. 5,617,857 (Chader, et al.) and 5,622,170 (Schulz) discussed previously. However the invention is not limited to this particular OTS, and other position tacking systems, such as sonic position detecting systems, may also be utilized.

As illustrated in FIG. 1, the surgical instrument 109 is elongated in shape, having a longitudinal axis and tip 115 pointing toward the tissues of interest. The instrument may be an endoscope having a conical field of view 116 that is indicated by dotted lines in FIG. 1. The instrument shown in the Figure is held at a position external to the patient's head. If an incision 118 has been made into the skull, the instrument may be inserted through the incision; this alternative position is shown by dotted lines in FIG. 1. In both positions the instrument is held so that there is an unobstructed line of sight between the LED's 110, 111 and the sensing unit 105. In endoscopic and other optical viewing applications, the instrument may include a laser targeting system (not shown in the drawings) to illuminate and highlight the region under examination.

Figure 2:
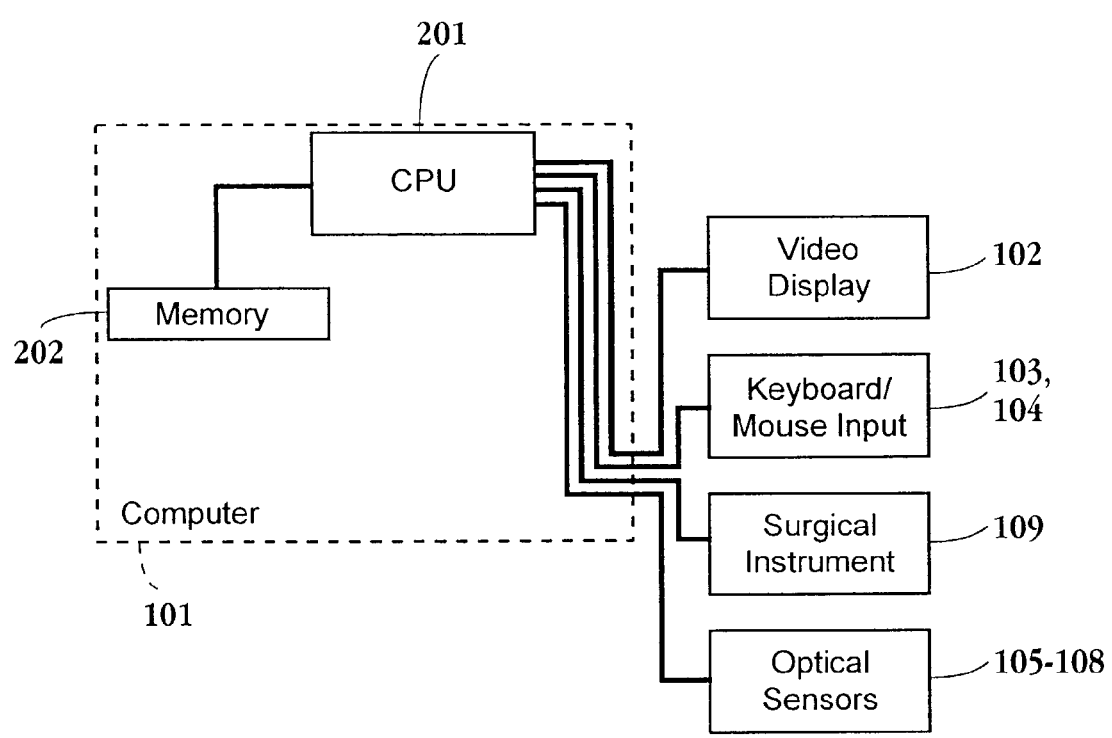
FIG. 2 is a schematic block diagram of the computer system and optical tracking system of the present invention.

FIG. 2 shows a schematic block diagram of the computer system connected to the position tracking system. The computer 101 includes a central processing unit (CPU) 201 communicative with a memory 202, the video display 102, keyboard and mouse 103, 104, optical detectors 106-108, and the LED's mounted on the surgical instrument 109. The computer memory contains software means for operating and controlling the position tracking system. In an alternative preferred embodiment, the OTS components 105-109 may be connected to and controlled by a separate computer or controller which is connected to the computer 101 and provides continual data indicating the position and orientation of the surgical instrument 109.

Figure 3:
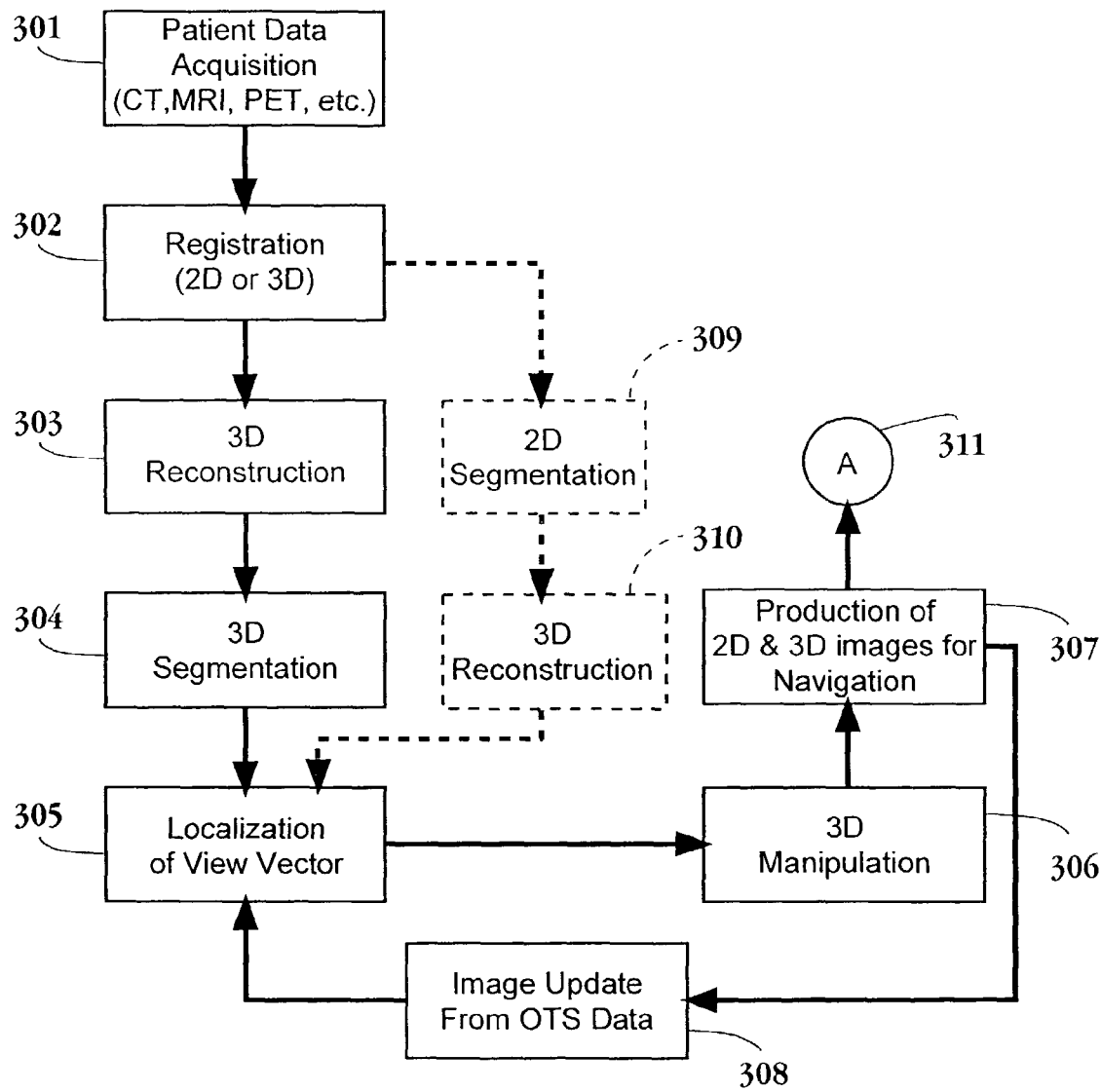
FIG. 3 is a schematic block diagram of the navigation protocol using pre-operative data that is followed in carrying out the method of the present invention.
Figure 4:
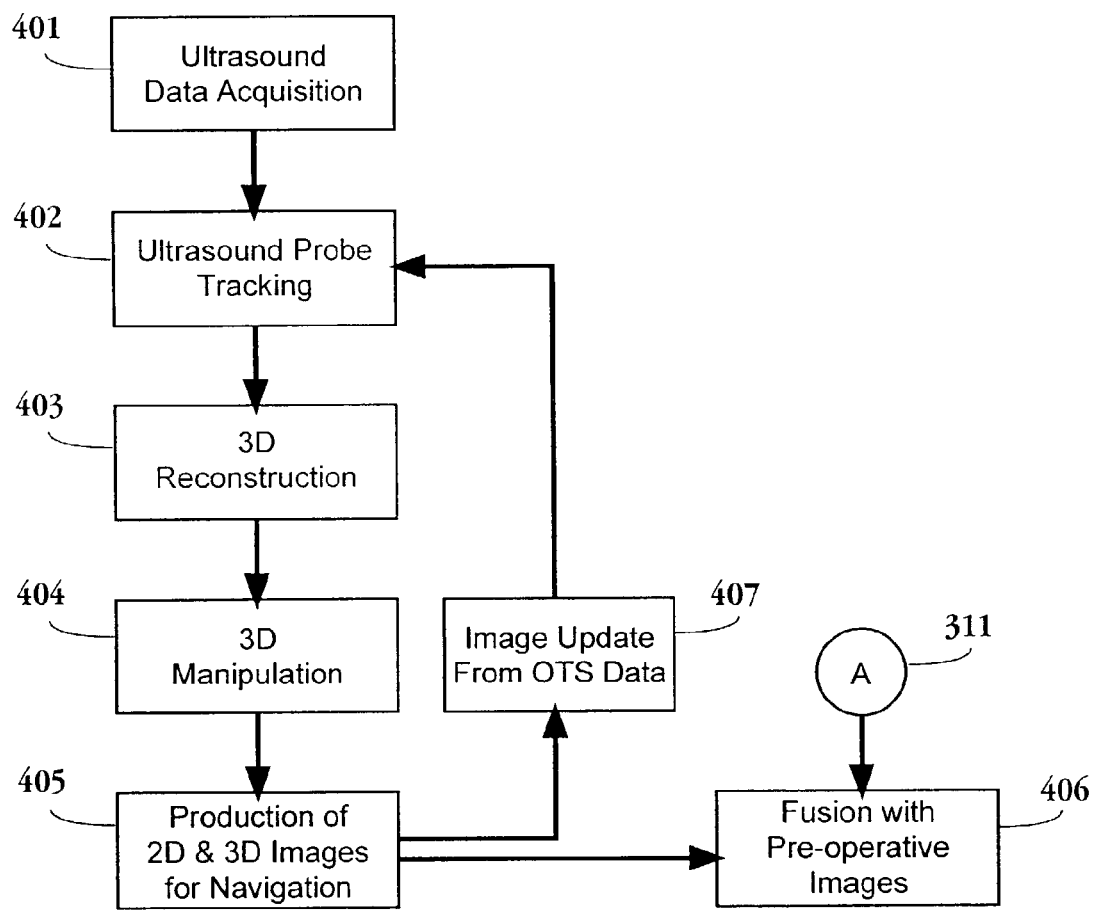
FIG. 4 is a schematic block diagram of the navigation protocol using ultrasound intra-operative data that is followed in carrying out the method of the present invention.
Figure 5:
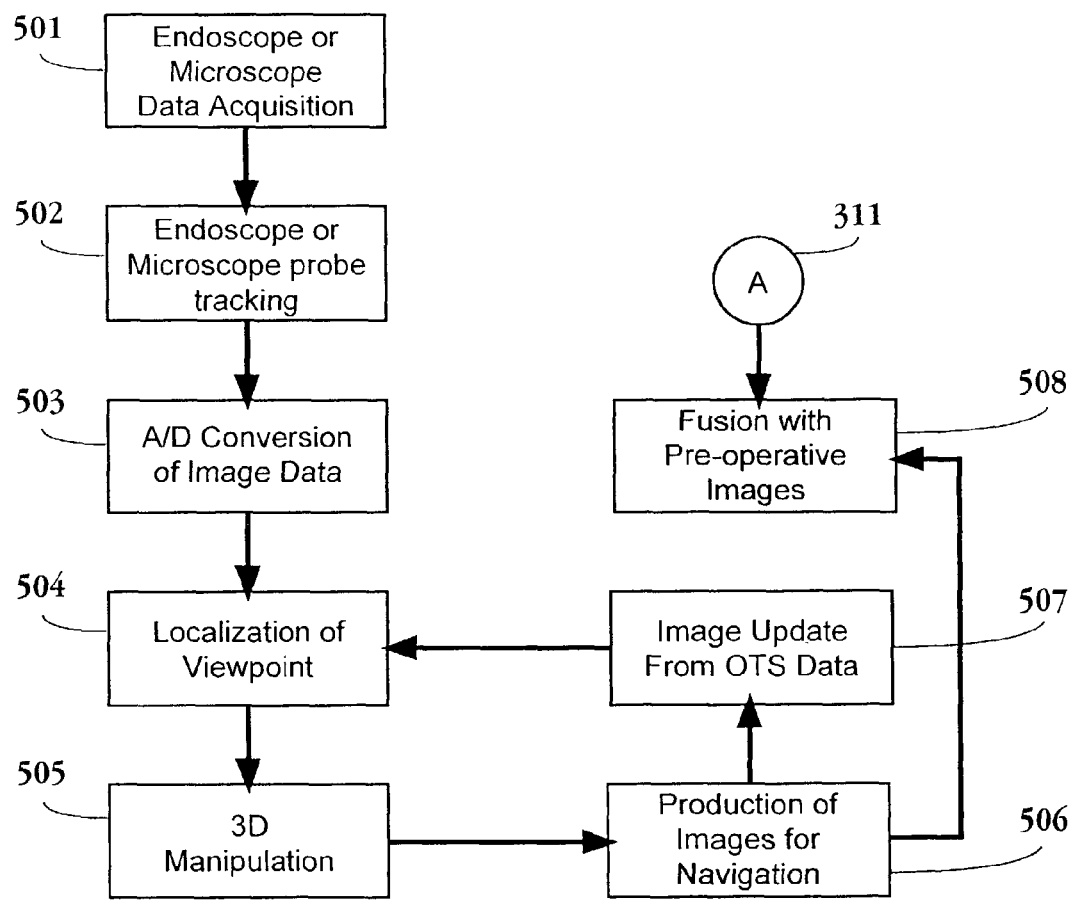
FIG. 5 is a schematic block diagram of the endoscopic protocol that is followed in carrying out the method of the present invention.

The above apparatus is operated to carry out surgical protocols that are illustrated schematically in FIGS. 3-5. FIG. 3 is a schematic block diagram of the protocol for handling pre-operative data ("pre-op protocol") to generate images during surgery according to the present invention. It is assumed that three-dimensional image data of the patient's head have been previously obtained from one or more of the techniques that are known to persons of ordinary skill in the medical imaging arts. Preferably these data are acquired from CT, MIR and/or MRI scan techniques to provide images with improved accuracy and detail, compared to ultrasound scan data for example. The scan data are loaded and stored 301 into the computer memory 202 through additional input means such as disk drives or tape drives, not shown in the drawings.

The patient data is registered 302 according to one of the generally known techniques. This procedure may be either a three-dimensional registration of the entire data set, or a slice-by-slice sequence of two-dimensional registrations. Following the three-dimensional registration, the image is reconstructed 303 in memory, using volumetric or surface rendering to produce an array of 3-dimensional voxel data. Segmentation 304 is then carried out on these data to distinguish various anatomical features, such as different types of material in the head (bone, brain tissue, vascular and ventricular structures, etc.) and the location of surfaces, using one or mox of known segmentation techniques. Preferably the segmentation process includes assigning different display colors to different types of structures to facilitate their identification and distinction in a color video display. For example, the vascular system may be displayed in red, the ventricular system may be shown in blue, bones may be colored brown, and so on. In a preferred embodiment these assignments may be varied by the user by means of the keyboard 103 or mouse 104. Also in a preferred embodiment the display opacities may be varied by the user by means of the keyboard 103, mouse 104, or other input device (such as a voice-activated device) to further facilitate their identification and distinction of hidden or obstructed features in the video display. In an alternative protocol in which 2-dimensional registration is carried out, segmentation 309 can be done for each 2-dimensional image sample, and the 3-dimensional data are then reconstructed 310 from the segmented data slices. This alternative protocol is shown by dotted lines in the Figure.

Referring still to FIG. 3, the next phase of the pre-op protocol is to determine the location and orientation of the view vector 305 to define the image to be displayed. This view vector is obtained by querying the OTS to ascertain the current location and orientation of the surgical instrument 109. With this information, the three-dimensional scan data is then manipulated 306 to position and orient the resulting three-dimensional perspective view and to define cutting planes and reference markers in the displayed image indicating and clarifying this view. The manipulated three-dimensional perspective image is then displayed 307 on the video display 102. In addition, other two-dimensional images, such as 2D sectional views for any cutting planes, are preferably also displayed along with the 3D perspective display for purposes of elucidation.

Finally, the pre-op protocol is a continuing loop process in which the OTS is repeatedly queried 308 for changes in the location of the view vector corresponding to changes in the position and orientation of the surgical instrument 109. Thus the displayed images are continually being updated during the surgical procedure, and the resulting displays are constantly refreshed in real time. The image data are also stored or buffered and made available for further use 311 according to subsequent protocols.

The surgical instrument 109 may include an ultrasound transducer located at the tip 115, which itself scans and detects ultrasound imaging data when placed in contact with the patient's head. FIG. 4 is a schematic block diagram showing the intra-operative ("intra-op") ultrasound ("US") protocol for handling the US image data during surgery. Typically the ultrasound transducer is a phased focusing array which generates data from a planar fan-shaped sector of the anatomical region of interest, where the central axis of the transducer lies in the plane of the scan sector which, in this context, is collinear with the longitudinal axis of the surgical instrument 109. By rotating the instrument and transducer about this axis, US scan data is collected and stored 401 for a cone-shaped volume in the region of interest. This cone defines the "field of view" of the transducer scan.

The location and orientation of the transducer is tracked and determined 402 by the OTS, and the US data is used to reconstruct 403 three-dimensional intra-op image data for the region of interest. This data is manipulated 404 in a way analogous to the manipulation 306 of the pre-op data, and then used to generate three-dimensional images 405, together with any desired corresponding two-dimensional images of the ultrasound data. These intra-op images are fused 406 with the pre-op images generated by the pre-op protocol 311, and the composite images are further displayed. Finally, the OTS is continually strobed 407, and the ultrasound images are constantly refreshed.

FIG. 5 is a schematic block diagram of the intra-op protocol in which an endoscope is placed at the tip 115 of the surgical instrument 109. This protocol is also applicable for procedures utilizing a surgical microscope in place of the endoscope. Image data is acquired 501, using a CCD camera or other known technique, representing a 2-dimensional image in a plane orthogonal to the line of sight of the endoscope or microscope, which in this context is the longitudinal axis of the surgical instrument 109. The location and orientation of the instrument is tracked and determined 502 by the OTS, and analog-to-digital ("A/D") conversion 503 is carried out on the data. The location of the viewpoint is determined 504 from the OTS data, and the endoscope or microscope image data is manipulated 505 to generate the desired image 506 for display. These intra-op images are fused 508 with the pre-op images generated by the pre-op protocol 311, and the composite images are further displayed. Finally, the OTS is continually strobed 507, and the images are constantly refreshed.

Figure 6:
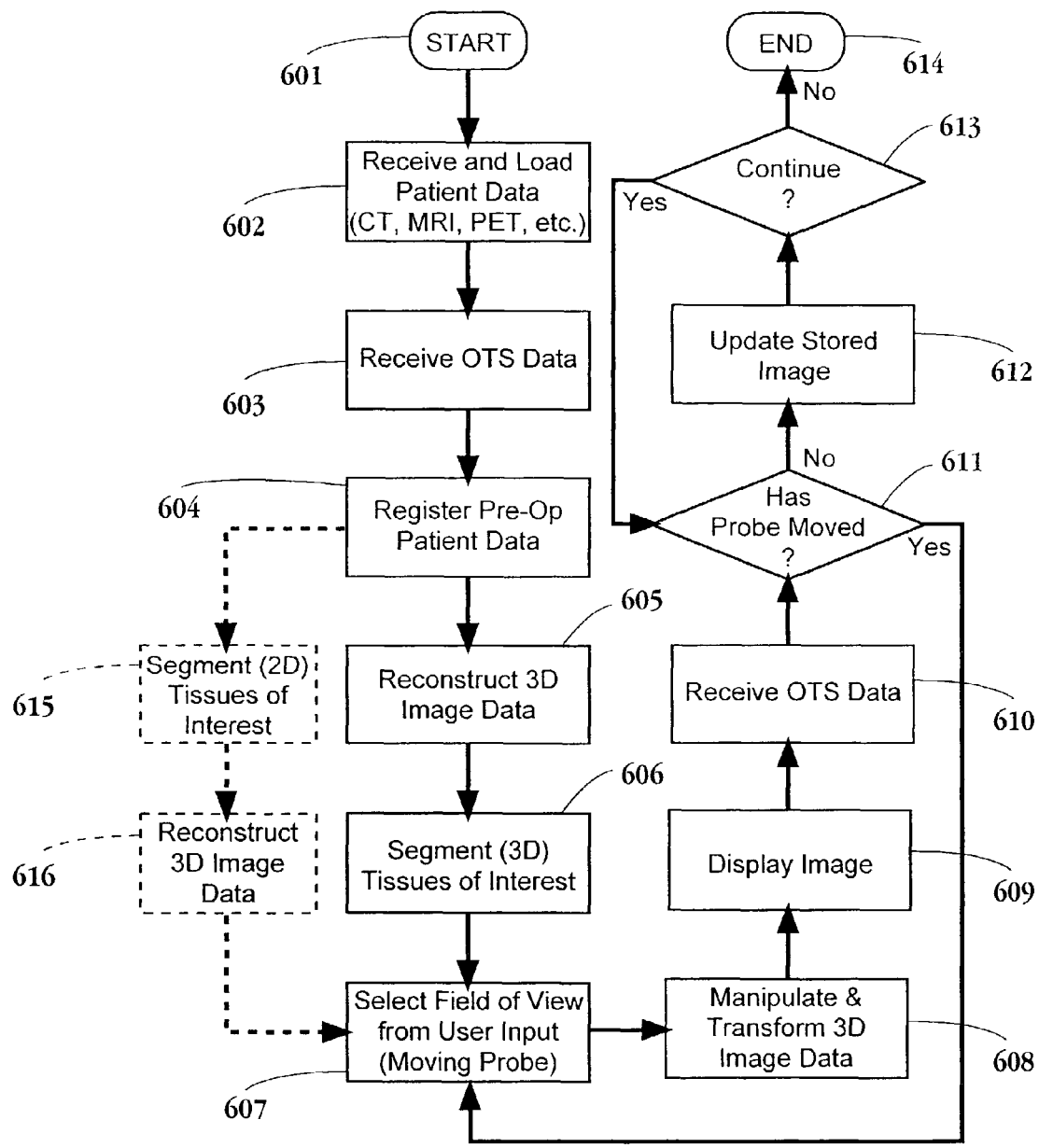
FIG. 6 is a schematic flow chart of the pre-operative computer program that implements the pre-operative protocol of the present invention.

The foregoing protocols are implemented by program modules stored in the memory 202 of the computer 101. FIG. 6 is a schematic block diagram of a flow chart for a program that implements the pre-op protocol. The program starts by causing the computer to receive and load 602 previously obtained scan data for the patient, such as MRI or CT data. The computer further reads data from the OTS 603 to register the scanned patient data 604. For 3D volumetric rendering, the scanned data is used to reconstruct image data 605 in three dimensions, and segmentation 606 is carried out on this reconstruction. In an alternative embodiment, shown by dotted lines in the Figure, segmentation is carried out on 2D slices 615, and these segmented slices are then reconstructed into the full 3D image data.

The program next reads input data from the keyboard 103 or mouse 104 to enable the user to select a field of view for image displays 607. The image data is then manipulated and transformed 608 to generate the requested view, along with any selected reference markers, material opacities, colors, and other options presented to the user by the program. In addition, the user may request a 3D display of the entire head, together with a superimposed cone showing the field of view for an endoscope, microscope, ultrasound transducer, or other viewing device being used during the surgery. The resulting manipulated image is then displayed 609 preferably in color on the video display 102. The computer next reads the OTS data 610 and determines 611 whether the surgical instrument has moved. If so, program control returns to the selection of a new field of view 607 and the successive operations 608-610 shown in FIG. 6. If the position of the instrument has not changed, the displayed image is stored 612, refreshing any previously stored display image. The program further looks for requests from the user 613 whether to discontinue operation, and it there are no such requests, the operations 611 and 612 are repeated. Thus the computer remains in a loop of operations until the user requests termination 614.

Figure 7:
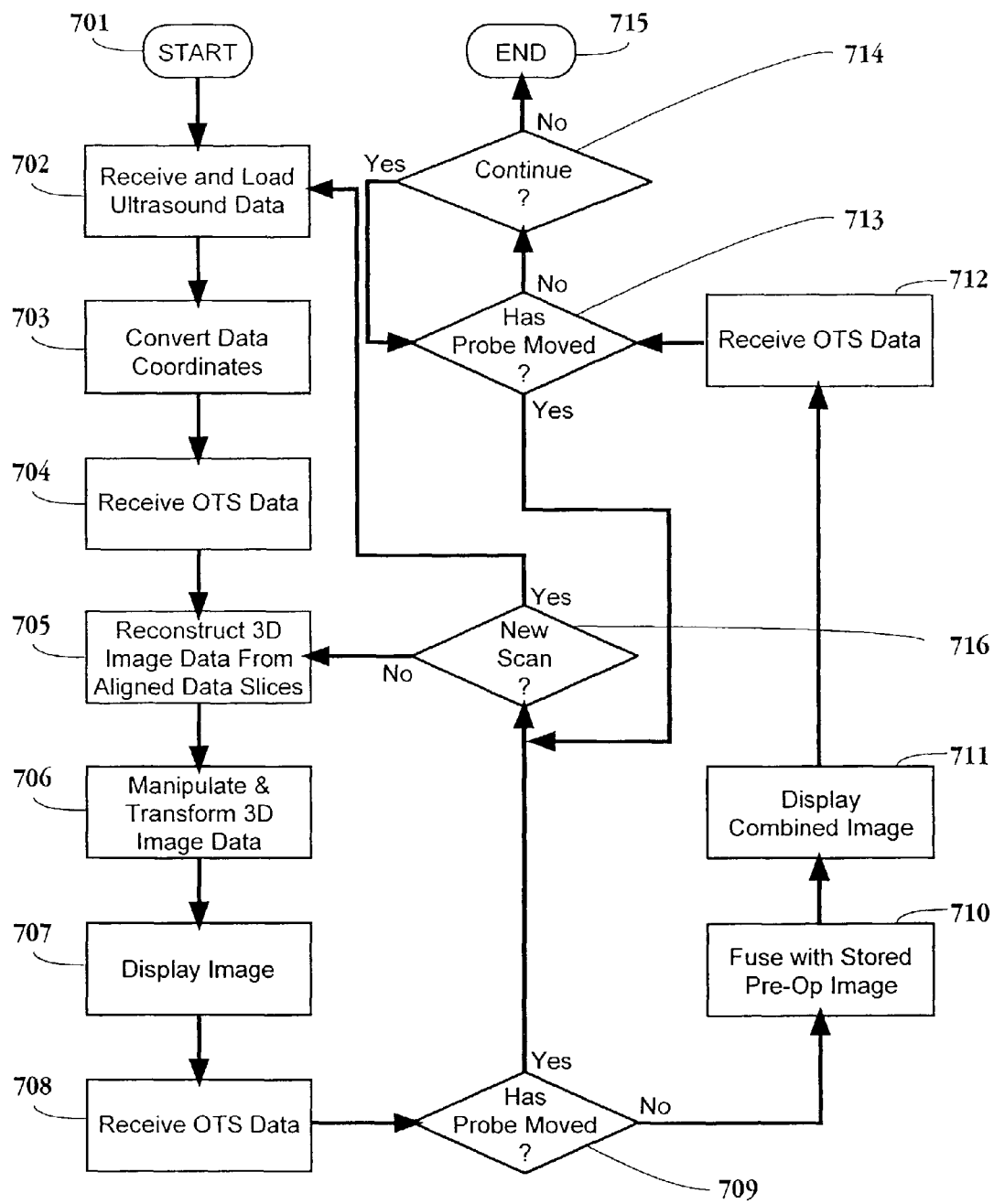
FIG. 7 is a schematic flow chart of the intra-operative ultrasound computer program that implements the ultrasound protocol of the present invention.

FIG. 7 is a schematic block diagram of a flow chart for a program that implements the ultrasound intra-op protocol. The program starts 701 by causing the computer to receive and load the data from a US transducer at the tip 115 of the surgical instrument 109. Such data is produced normally using polar or spherical coordinates to specify locations in the region of interest, and the program converts 703 this data preferably to Cartesian coordinates. Next, OTS data is read 704 to determine the position and orientation of the surgical instrument 109, and US data from the aggregation of aligned data slices is utilized to reconstruct 3D image data 705 representing the US scan data. This image data is manipulated and transformed 706 by the program in a manner similar to the manipulation 608 of the pre-op data 608, and the resulting image is displayed 707.

Similarly to the pre-op program shown in FIG. 6, the OTS is queried 709 to determine whether the surgical instrument has moved 713, and if so a new US display image is constructed. In a preferred embodiment, the program queries the user 716 whether to carry out another US scan of the region of interest. If so, program control returns to the operation 702 in FIG. 7 and fresh US data is obtained by the US transducer. If another scan is not requested 716, the program returns to operation 705 and a new 3D image is reconstructed from the present US scan data.

If the OTS query 709 determines that the surgical instrument has not moved since the last query, the US image is fused 710 with the pre-op image obtained by the program shown in FIG. 6, and the combined image is displayed 711. The OTS is again queried 712 to determine 713 whether the surgical instrument has moved. If so, the program returns to the new scan user query 716. Otherwise the program further looks for requests from the user 714 whether to discontinue operation, and if there are no such requests, the operation 713 is repeated. Thus the computer remains in a loop of operations until the user requests termination 715, similarly to the pre-op program of FIG. 6.

Figure 8:
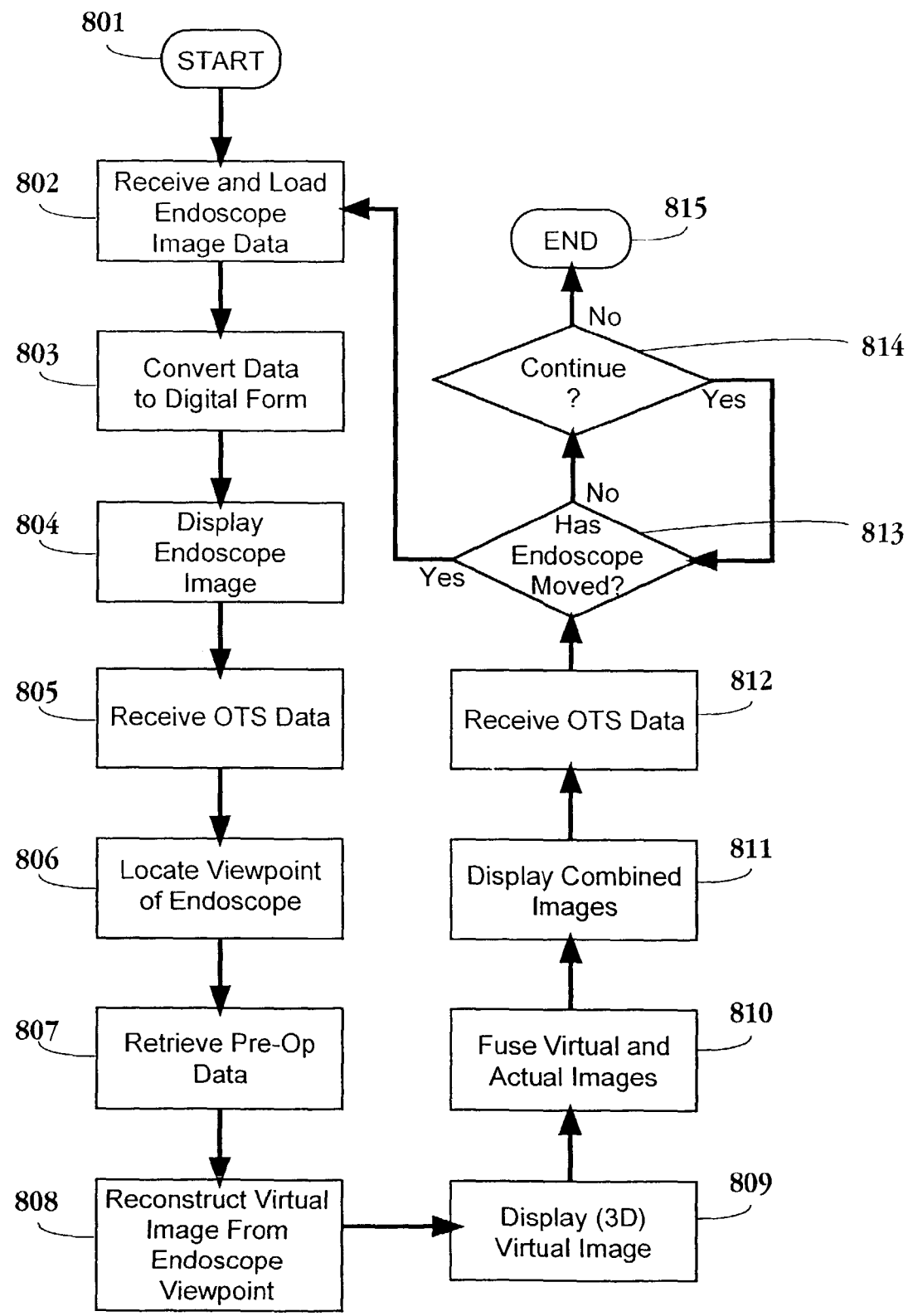
FIG. 8 is a schematic flow chart of the intra-operative endoscope computer program that implements the endoscope protocol of the present invention.

The endoscope/microscope intra-op protocol is implemented preferably by the endoscope intra-op program having a flow chart shown in schematic block diagram form in FIG. 8. Upon starting 801, the program causes the computer to receive and load image data from the endoscope 802. This data is digitized 803 and preferably displayed 804 on the video display 102. The OTS is queried 805 to receive information determining the location and orientation of the endoscope 806. Using this information, the pre-op data obtained by the pre-op program illustrated in FIG. 6 is retrieved 807, and utilized to reconstruct a 3-dimensional virtual image 808 from the viewpoint of the endoscope. This image is displayed 809, in a manner similar to the 3D display of images by the pre-op program illustrated in FIG. 6. This image is fused 810 with the endoscope image displayed in operation 804, and the combined image is also displayed 811. The OTS is then strobed 812 to determine 813 whether the endoscope has moved since the last query, and if so, program control returns to the operation 802 which refreshes the image data received by the endoscope. Otherwise the program further looks for requests from the user 814 whether to discontinue operation, and if there are no such requests, the operation 813 is repeated. Thus the computer remains in a loop of operations until the user requests termination 815, similarly to the pre-op and intra-op programs of FIGS. 6 and 7.

The foregoing program modules may be designed independently, and they can be configured also to run independently. Thus, the pre-op program may be completed, followed by running of either or both of the intra-op programs. Preferably, however, these programs operate in parallel during surgery so that the pre-op data images and intra-op data images are all continually refreshed as the operation proceeds. Known methods for parallel execution of programs may be utilized to accomplish this result.

The above programs are carried out preferably on a computer 101 that is adapted for computer graphics applications. Suitable computers for these programs are commercially available from Silicon Graphics, Inc. of Mountain View, Calif. Graphics software modules for most of the individual image processing operations in the above programs are also available from Silicon Graphics, Inc. as well as other sources.

Figure 9:
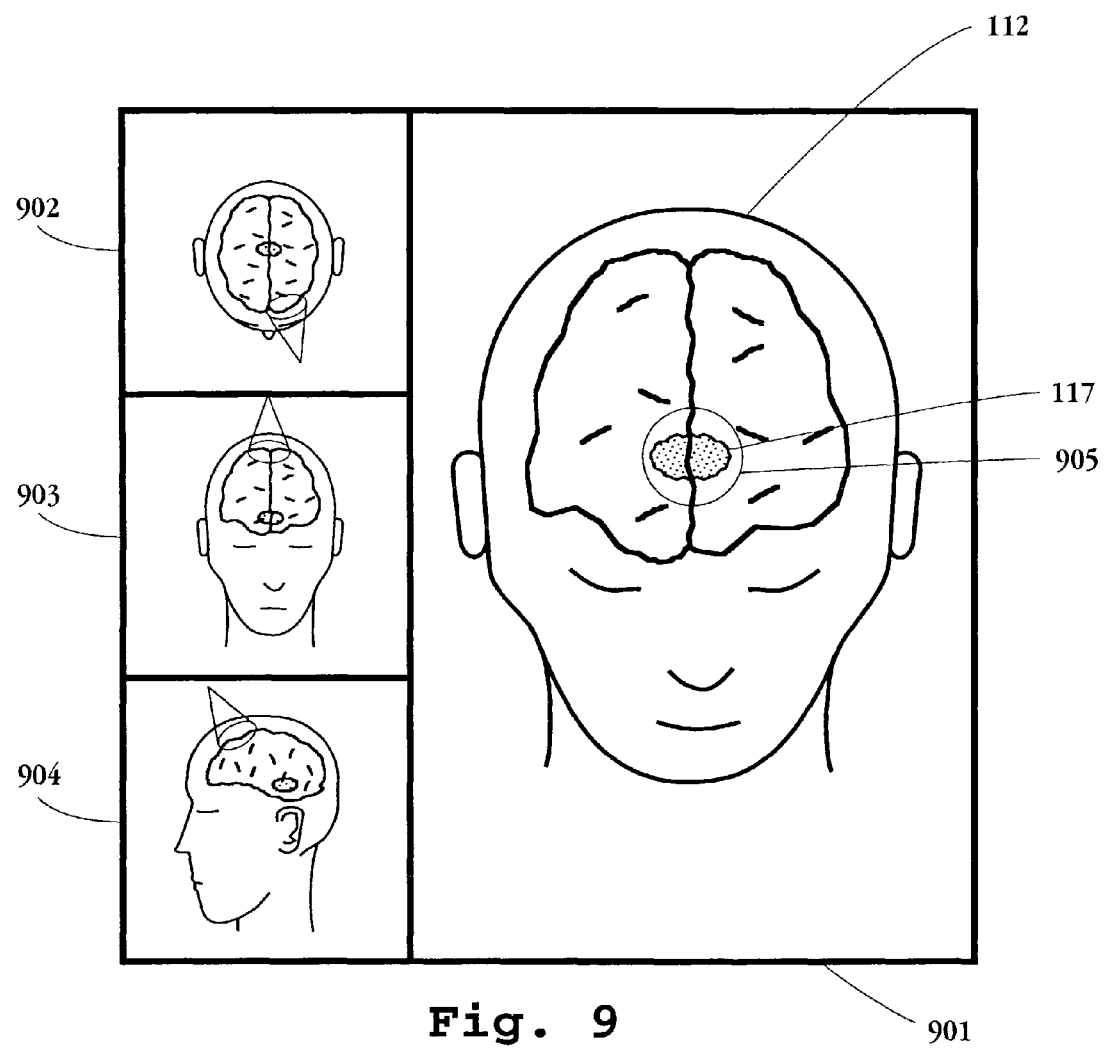
FIG. 9 is a drawing of a display generated according to the present invention, showing axial, coronal, and sagittal views of a head, together with a three-dimensional perspective view of the head taken from an exterior viewpoint.

Referring now to FIG. 9, the drawing shows a highly simplified sketch of a three-dimensional image-display 901 obtained by the above system with the surgical probe 109 of FIG. 1 in the position illustrated, pointing toward the target lesion or tumor 117 inside the patient's head 112. The display 901 is a perspective view from the tip 115 of the probe 109 in FIG. 1. This display is continuously refreshed, so that as the probe 109 is moved the displayed image 901 immediately changes. It will be noted that, although the probe 109 in FIG. 1 is shown entirely outside the patient's head, the display 901 shows internal anatomical structures such as the brain and the target lesion 117. With the present system, the display characteristics can be adjusted in real time to emphasize or de-emphasize the internal structures. These structures may be distinguished by displays with different colors for different types of material. Also, the display opacity of the skin, skull, and brain tissue may be reduced to provide or emphasize further structural details regarding the target lesion 117. In short, the display 901 effectively equips the surgeon with "X-ray eyes" to look at hidden structures through obstructing surfaces and objects. With this display, the entire internal structure of the head may be examined and studied to plan a surgical trajectory before any incision is made. Furthermore, if the surgical instrument 109 in FIG. 1 is a scalpel, the display 901 allows the surgeon to see any structures immediately behind a surface prior to the first incision. FIG. 9 shows also the conventional axial 902, coronal 903 and sagittal 904 2D displays for purposes of further clarification and elucidation of the region under examination.

When the surgical instrument 109 is an endoscope or US transducer, the field of view 116 is also indicated in the display 901 by the quasi-circular image 905 indicating the intersection of the conical field of view 116 with the surface of the skin viewed by the endoscope 109. This conical field of view is also superimposed, for completeness, in the 2D displays 902-904. In a preferred embodiment, displays are also presented showing the actual image seen by the endoscope in the field of view 905, and the 3D perspective image for the same region in the field of view 905; these auxiliary displays are not shown in the drawings. Similar auxiliary displays are preferably included when the instrument 109 is an ultrasound transducer.

Figure 10:
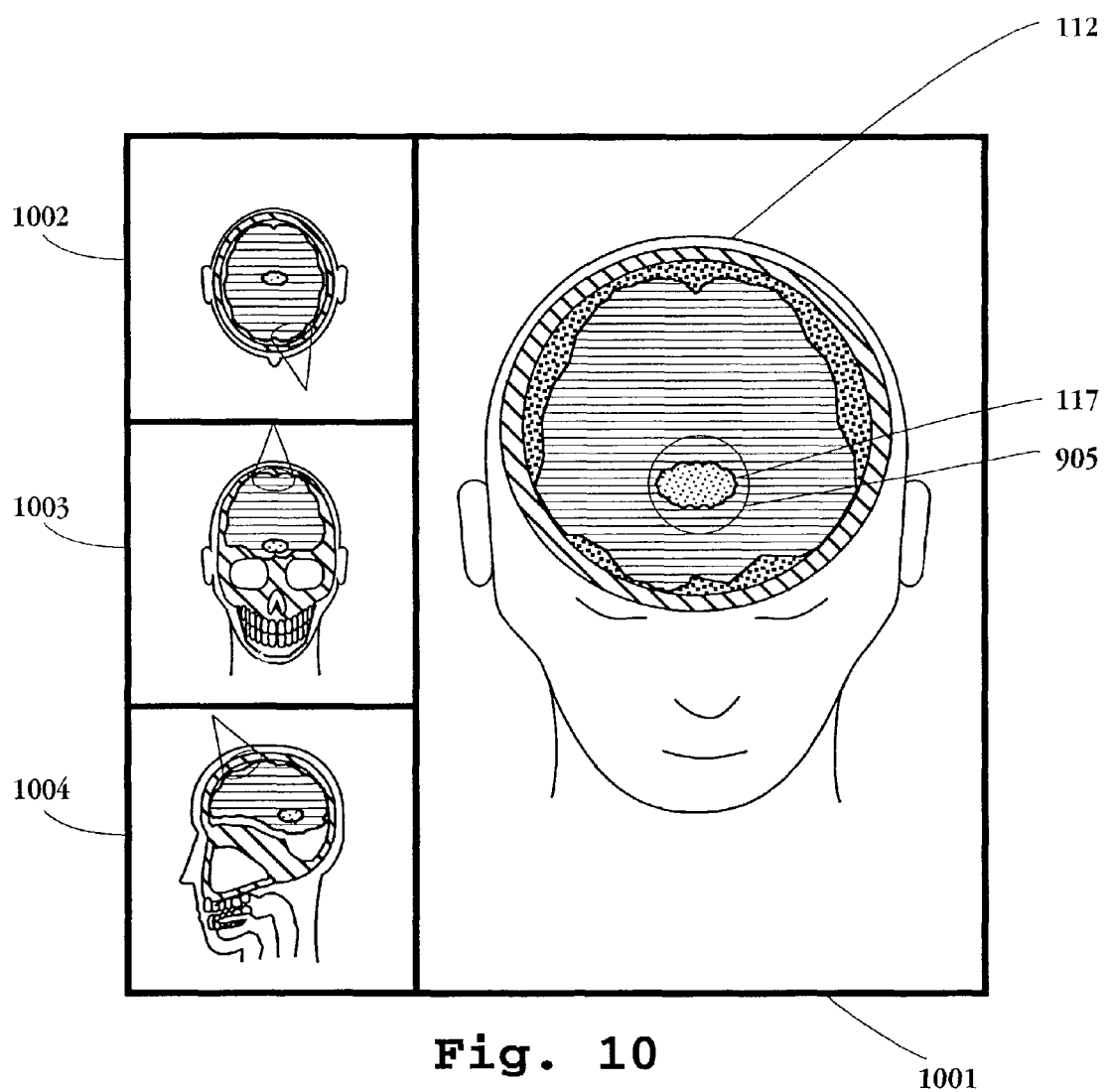
FIG. 10 is a drawing of a display generated according to the present invention, showing sectional axial, coronal, and sagittal views of a head, together with a three-dimensional perspective view of the head taken from an interior viewpoint.

After an incision 118 has been made in the patient's head, the endoscope may be inserted to provide an internal view of the target anatomy. Referring now to FIG. 10, the drawing shows a highly simplified sketch of a three-dimensional image display 1001 obtained by the above system with the endoscope 109 of FIG. 1 in the alternative position shown by the dotted lines, pointing toward the target lesion or tumor 117. The display 1001 has been manipulated to provide a three-dimensional sectional view with a cutting plane passing through the tip 115 of the endoscope 109 and orthogonal to its axis. Again, the endoscope field of view 905 is indicated in the display, and in a preferred embodiment auxiliary displays are also presented showing the actual image seen by the endoscope in the field of view 905, and the 3D perspective image for the same region in the field of view 905; these auxiliary displays are also not shown in FIG. 10. This Figure further preferably includes also the conventional axial 1002, coronal 1003 and sagittal 1004 2D displays for purposes of further clarification and elucidation.

Figure 11A:
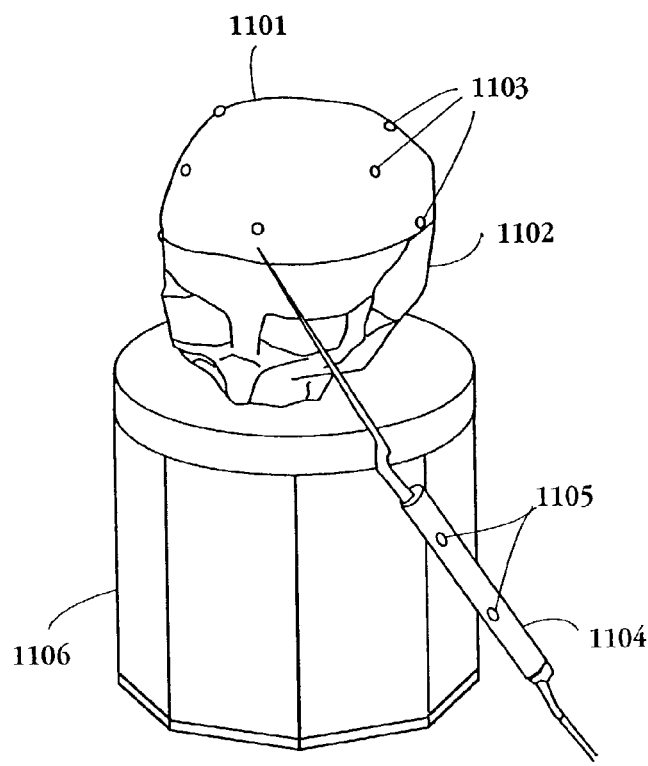
FIG. 11a is a drawing of a plastic model of a human skull and a surgical probe that has been used to demonstrate the present invention.
Figure 11B:
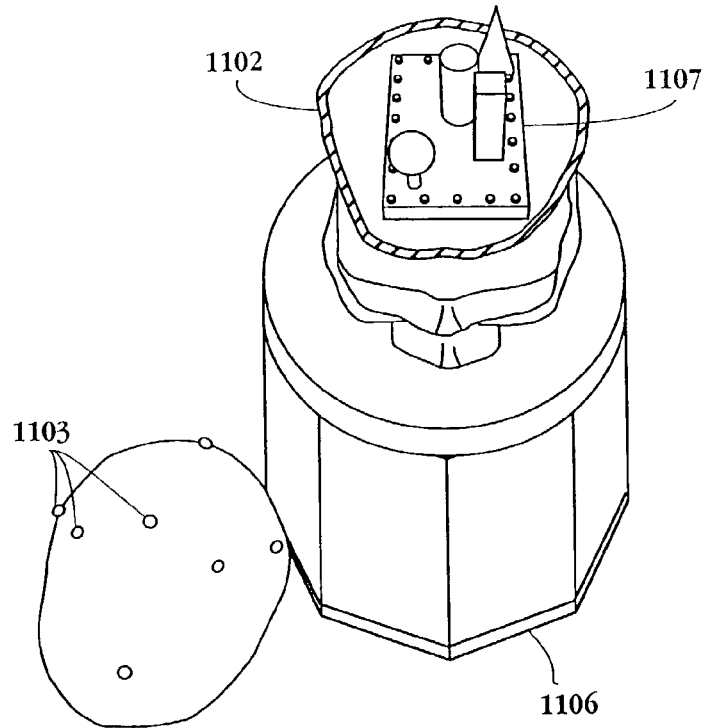
FIG. 11b is another drawing of the model skull of FIG. 11a, with the top of the skull removed to show model internal structures for demonstration purposes.
Figure 12A:
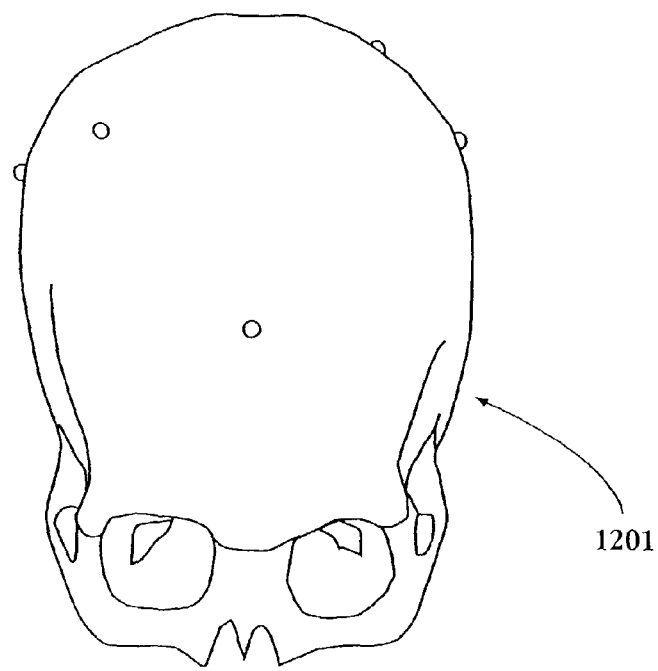
FIGS. 12a and 12b are simplified reproductions of two displays produced by the present invention for the model skull shown in FIGS. 11a and 11b.
Figure 12B:
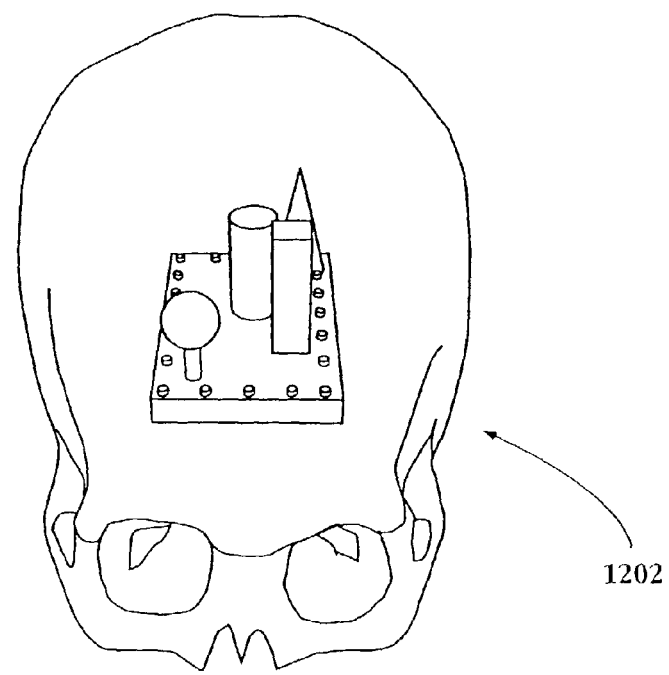

FIGS. 11a, 11b, 12a-b and 13a-b illustrate further the three-dimensional displays that are produced by a preferred embodiment of the present invention. Referring to FIGS. 11a, 11b, and plastic model of a skull has been fabricated having a base portion 1102 and a removable top portion 1101. These Figures show the model skull 1101, 1102 resting on a stand 1106. FIG. 11a also shows a pointer 1104 with LED's 1101 connected to an OTS (not shown in the drawing) that has been used to generate displays according to the invention. A plurality of holes 1103 in the top portion 1101 are provided, which allow the pointer 1104 to be extended into the interior of the skull. FIG. 11b shows the skull with the top portion 1103 removed. A plastic model of internal structures 1107 is fabricated inside the skull; these internal structures are easily recognizable geometric solids, as illustrated in the Figure.

The skull of FIGS. 11a, 11b has been scanned to generate "pre-op" image data, which has been utilized to produce the displays shown in FIGS. 12a-b, and 13a-b. FIG. 12 is a composite of two displays 1201, 1202 of the skull with the pointer 1104 directed toward the skull from a top center external location, similar to the location and orientation of the pointer shown in FIG. 1. The display 1201 is a three-dimensional perspective view from this pointer location. The display 1202 is the same view, but with the display opacity of the skull material reduced. This reduced opacity makes the internal structure 1107 clearly visible, as shown in the Figure. During actual use, the system enables the surgeon to vary this opacity in real time to adjust the image so that both the skull structure and the internal structure are visible in the display in various proportions.

It will be noted that the surface contour lines shown in the display 1201 are produced by the finite size of the rendering layers or voxels. These contour lines may be reduced by smoothing the data, or by reducing the sizes of the voxels or layers.

Figure 13A:
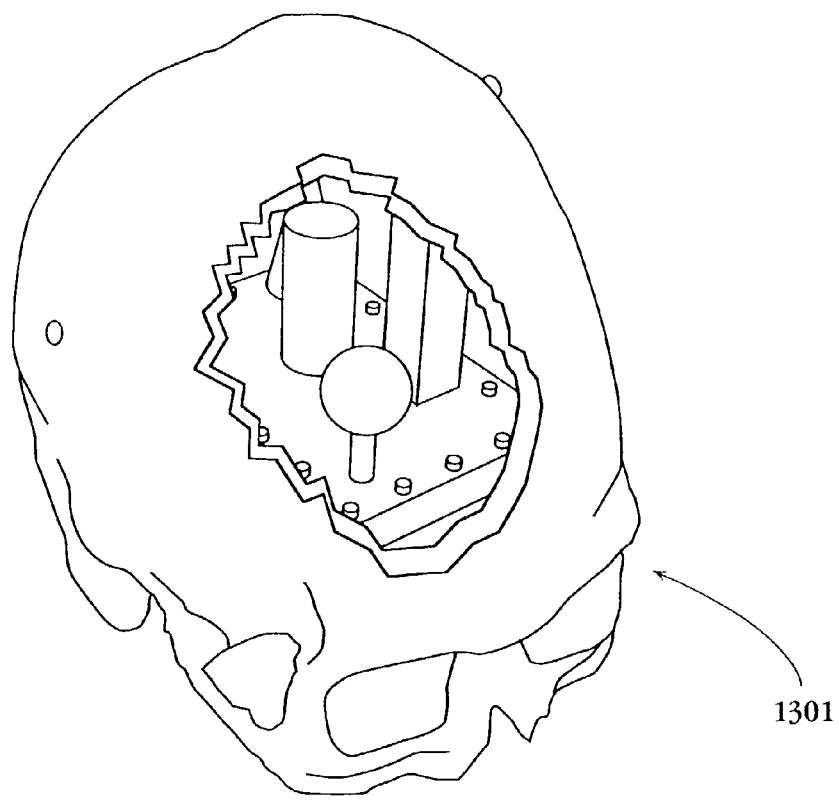
FIGS. 13a and 13b are simplified reproductions of two further displays of the invention for the skull in FIGS. 11a and 11b.
Figure 13B:
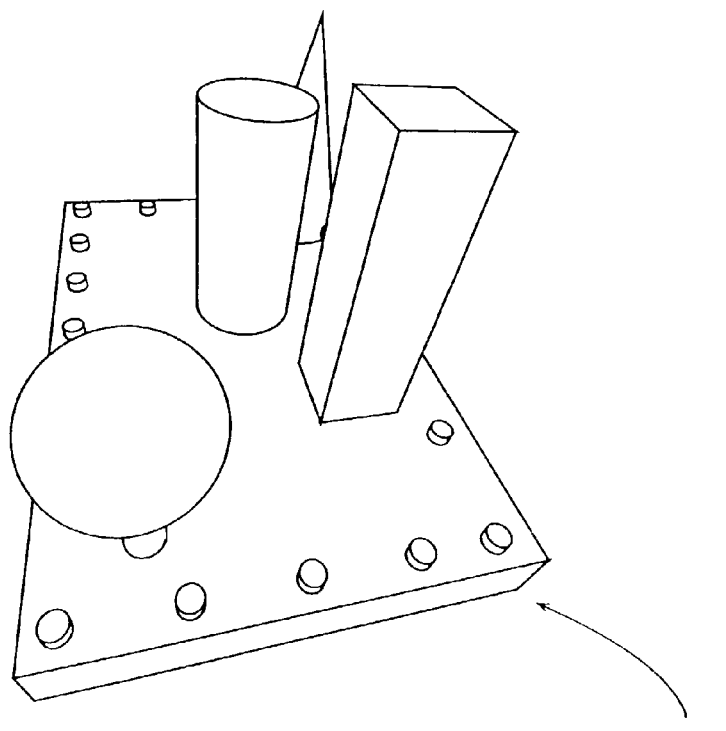
Figure 14B:
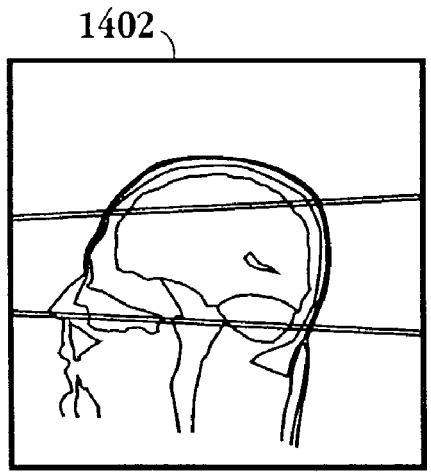
FIGS. 14a through 14i are reproductions of a composite display produced by the present invention for an actual human head.
Figure 14C:
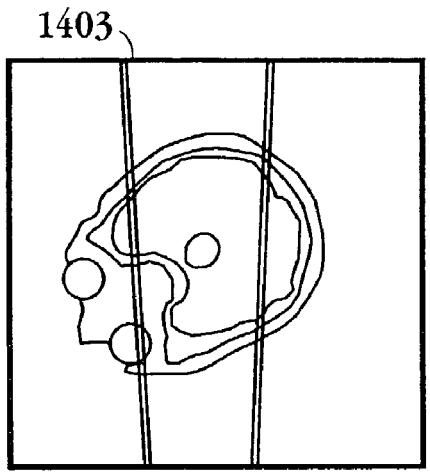
Figure 14A:
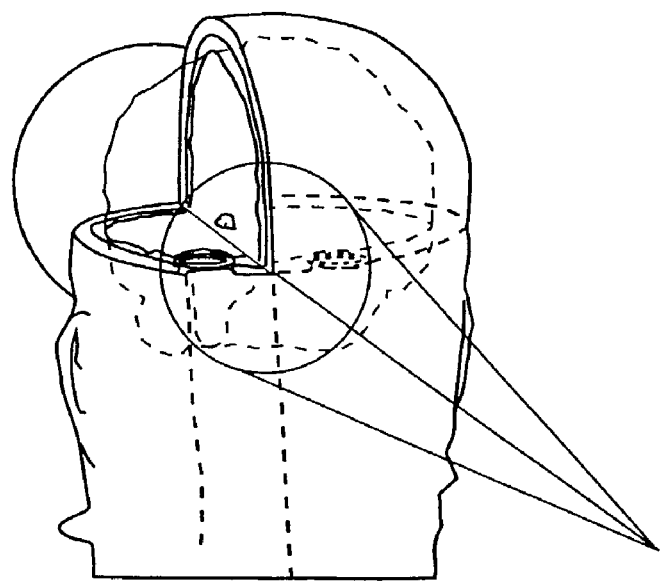
Figure 14D:
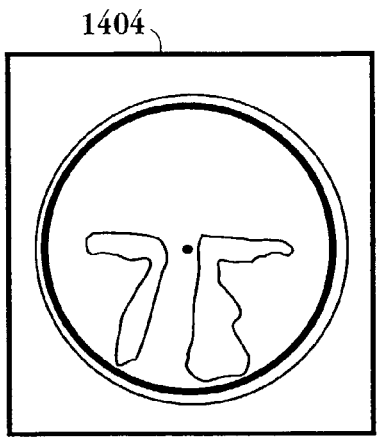
Figure 14E:
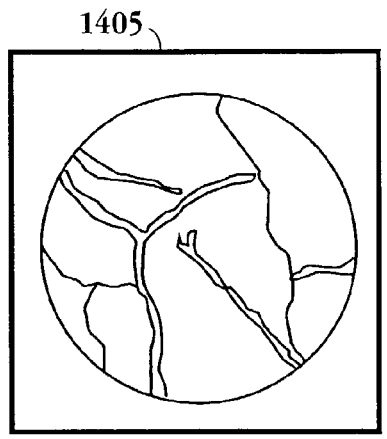
Figure 14F:
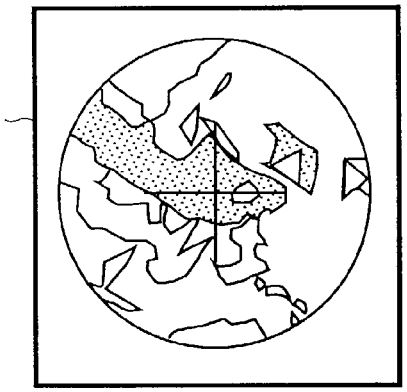
Figure 14G:
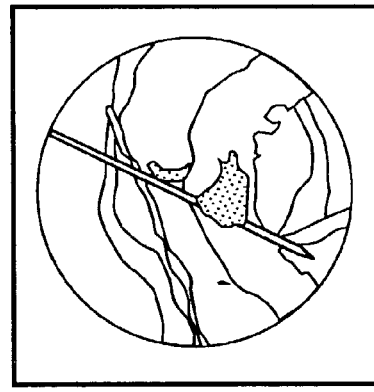
Figure 14H:
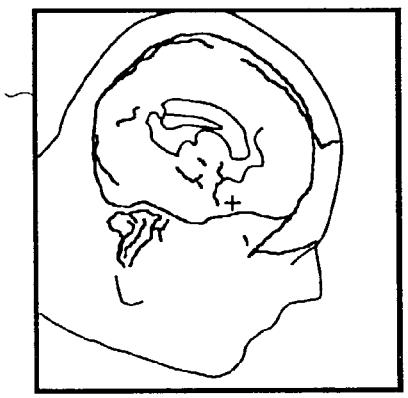
Figure 14I:
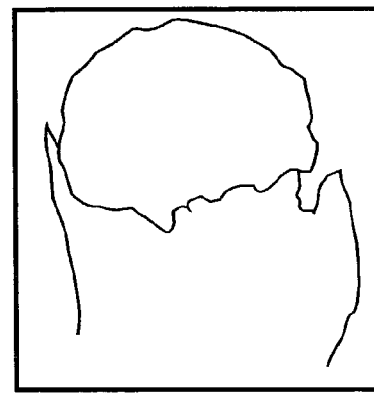

FIGS. 13a-b are composites of two further displays with the pointer 1104 moved to extend through one of the openings 1103. Display 1302 is the view from the tip of the pointer inside the skull. Display 1301 is a view of the entire structure from outside the skull along the pointer axis; in other words, display 1302 is substantially a magnification of part of display 1301. Display 1301 shows the skull with a portion cut away by a cutting plane through the tip of the pointer, perpendicular to the pointer axis. Both of these displays clearly illustrate the perspective nature of the three-dimensional displays generated by the present invention.

FIGS. 14a-i are simplified composites of displays generated by the system for an actual human head. Display 1401 is a perspective view of the entire head with a cutaway portion defined by orthogonal cutting planes as shown. This display also shows the field of view of an endoscope pointing toward the head along the intersection line of the two cutting planes, with the tip of the endoscope at the apex of the cone. Display 1402 shows the two-dimensional sectional view produced by the vertical cutting plane, and display 1403 shows the corresponding sectional view produced by the horizontal cutting plane. Furthermore, the images in displays 1402 and 1403 are also transformed (rotated and magnified) and superimposed on the three-dimensional image in display 1401.

Both of these displays indicate also the intersection of the cutting planes with the conical field of view. Display 1404 is the actual image seen by the endoscope. Display 1405 is a virtual perspective view of the endoscope image reconstructed from scan data by volume rendering in accordance with the present invention. Display 1406 is a virtual perspective view of the image from the endoscope viewpoint with a narrower field of view, reconstructed from scan data by surface rendering in accordance with the present invention. This display 1406 would be used with a surgical probe in planning a surgical trajectory. Display 1407 is a magnification of 1406 (i.e. with a narrower field of view) showing the virtual image that would be seen through a microscope. Finally, display 1408 is a segmented three-dimensional perspective view of the entire head from the scan data utilizing surface rendering, and display 1409 is the same view with volume rendering. FIG. 14 illustrates the rich variety and versatility of the displays that are possible with the present system. All of these displays are presented to the surgeon in real time, simultaneously, and can be varied on line.

Another embodiment of the present invention provides neurosurgeons with the ability to visualize the surgical microscope's field of view, overlaid with the segmented, volumetric-images, for any localized area on the patient's anatomy. This allows the surgeon to continually investigate the outcome of each step of the surgery. This embodiment can be implemented as an addition to the modern stereotactic techniques using a common frame of reference. As previously described, such reference frames, or fiducial markers, register the patient's anatomy with the 3D-image in an ongoing surgical process.

In one embodiment software can be dedicated for localizing a surgical microscope's field of view in 3D-space and then superimposing upon it previously acquired 3D-imaging data. Using this 3D-navigation system, the surgeon can visualize the surgical site while exploring the inner-layers of the patient's anatomy. A laser targeting system and video cameras are used to increase the contrast of various tissue elements and to optimize the location of the surgical site. The ability of the stereo-vision cameras to locate a point in space allows for the tracking of moving objects in relation to that point. The 3D coordinates of surgical instruments can be calculated and thus their spatial relationship to the target lesion can be extrapolated as real-time changes occur.

As described herein, the patent's anatomy data is registered using techniques known to one in the art. Previously acquired images gained through techniques including magnetic resonance imaging, computer tomography, and positron emission tomography, can be combined with a microscope's field of view. Fiducial markers are placed on the patient's anatomy in such a manner so as to remain within the field of view of the 3D imaging data. Using these fiducial markers and a standard Cartesian Coordinate System, the position of an area of interest can be determined in 3D-space relative to the fiducial markers.

The same area of interest can be examined real-time using a surgical microscope. A laser targeting system outlines the surgical microscope's field of view on the patient's anatomy and communicates data identifying this field of view to a processor. The laser targeting device can be made up of a class-two, 0.3 mw (not harmful to human tissue) laser diode and mirror galvanometers (the latter are electro-mechanical devices which rapidly rotate a small mirror). In one embodiment, two of these lasers are mounted at right angles to each other and configured to move a bright spot to arbitrary positions on a projection surface. Typically, the pattern developed by the laser depends on frequency and voltage where frequency controls the shape of projection, and voltage controls the size of the pattern. The laser system can be mounted on top of the surgical microscope so that the laser pattern can be aligned with the microscope's field of view.

The computer reconstruction of the laser pattern's field view, and thus microscope's field of view, can be accomplished, in one embodiment, using second order ellipsoidal momentum equations. Using this method an arbitrary shape can be described and saved as its elliptical characteristics. Thus, any region can be defined from its moments. The first-order moment has three driven constants and the second-order model has three interrelated moments which combined define an ellipse.

Reconstruction of the laser pattern by the processor can be accomplished using a stereo-vision approach. This method requires multiple cameras to observe the procedure. Typically, two cameras are used to reconstruct the laser pattern and the spatial coordinates of the surgical trajectory device. Another pair of cameras calculates the spatial coordinates of the laser source.

Figure 15:
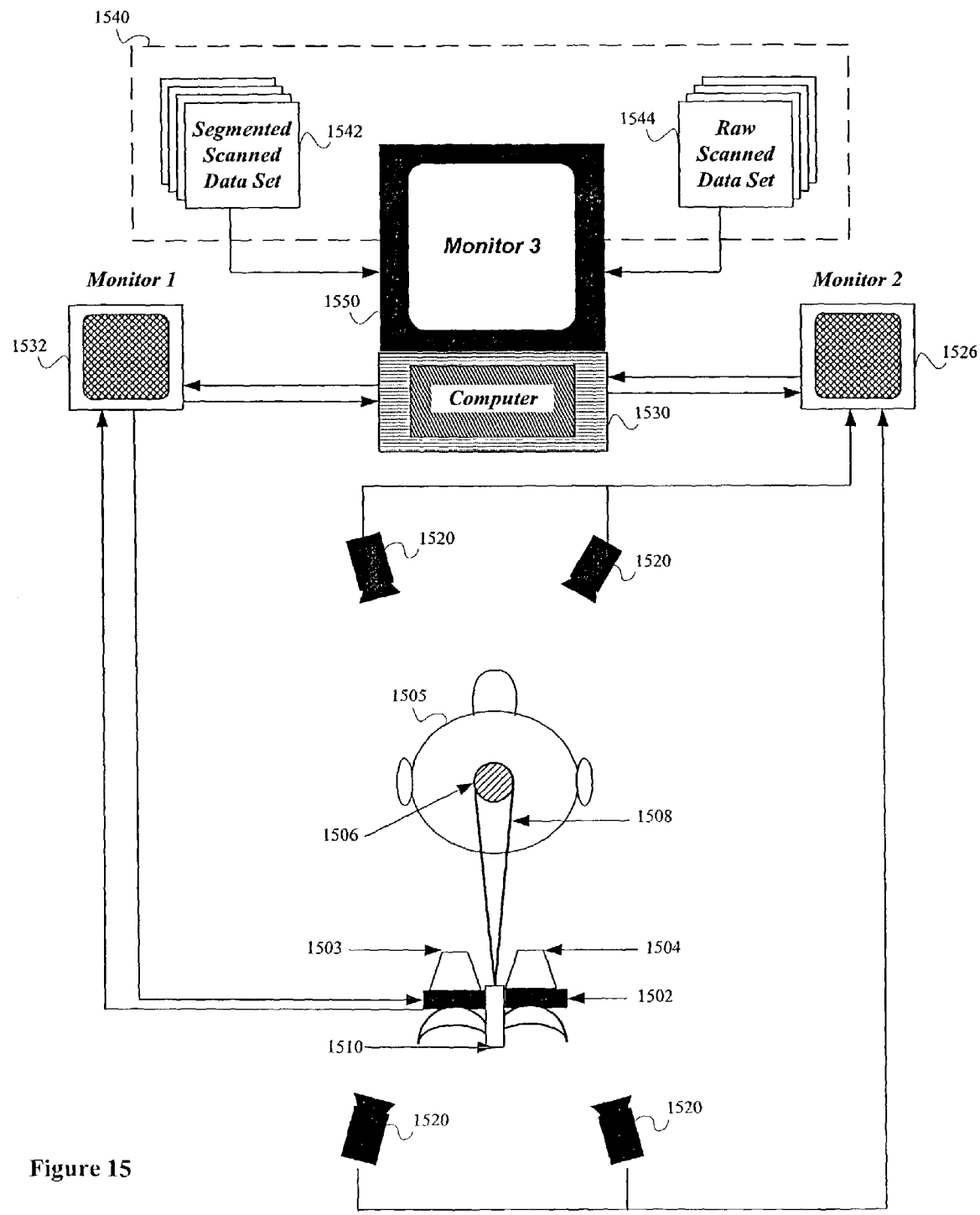
FIG. 15 is a schematic block diagram of a system for visual augmentation of stereotactic surgery.

FIG. 15 shows one embodiment of a system 1500 for combining real time imagery from a surgical instrument and pre-registered scanned data. A surgical microscope 1502, or similar surgical instrument, having a first eyepiece 1503 and a second eyepiece 1504, is positioned to view a portion of a patient's anatomy 1505 that has been pre-registered with scanned imagery. In the depiction of FIG. 15, the surgical microscope 1502 is positioned to view a portion of a patient's skull while in alternate embodiments other portions of a patients anatomy may be observed. The surgical microscope's 1502 field of view 1506 is outlined by a laser projection 1508. The projection emanates from a laser scanner 1510 mounted to, and aligned with the surgical microscope 1502. The laser projection 1508 and patient anatomy 1505 are monitored by four cameras 1520. The cameras 1520 are arranged in pairs such that each camera's 1520 field of view observes the patient's anatomy from a different vantage point. The cameras 1520 detect, identify, and monitor the movement of the patient's anatomy 1505, the laser projection 1508, and any other surgical instruments 1522 that may be present in the cameras' field of view. In an alternative embodiment the devices in the cameras' field of view can be color coded to aid in detection and identification. The cameras 1520 are coupled among a camera monitor 1526 and a processor 1530. The surgical microscope 1502 is coupled among a microscope monitor 1532 and the processor 1530. Pre-registered scanned data 1540, including raw scanned data 1542 and segmented scanned data 1544, is also coupled to the processor 1530. A third monitor 1550 displays an overlaid representation of the volumetric visualization of the pre-registered scanned data 1540 and the reconstructed microscope's field of view 1506. The microscope 1502, which is coupled to the processor 1530, displays an enhanced see-thru volumetric view of the pre-registered scanned imagery data 1540 in the first eyepiece 1503, while the second eyepiece 1504 displays a real-time view of the patient's anatomy 1505.

The third monitor 1550 provides a single display of all available information needed to predict an incision's trajectory. The surgeon, using this information, can move an insertion device around the surgical site to find the best optimal path to a lesion. Once the lesion is pinpointed and the path is free of obstacles, an incision can be made. In one embodiment the path of incision can be magnified for better targeting. At every step of the incision, the surgeon can view a monochromic slice that lies orthogonal to the tip of the incision device for precise cutting.

In addition, by using the surgical microscope 1502, the surgeon can monitor every step of the incision as he or she moves through the tissue. The distance that the incision device has traveled through the tissue is displayed as is a birds-eye view of the data set. This volumetric image can be seen from any direction and can be enlarged at the surgeon discretion. The surgeon can make arbitrary cuts through the volume to visualize the structures behind every surface, and "'fly thru" the volume to reveal the shapes and positioning of the segmented abnormalities before making an incision.

Figure 16:
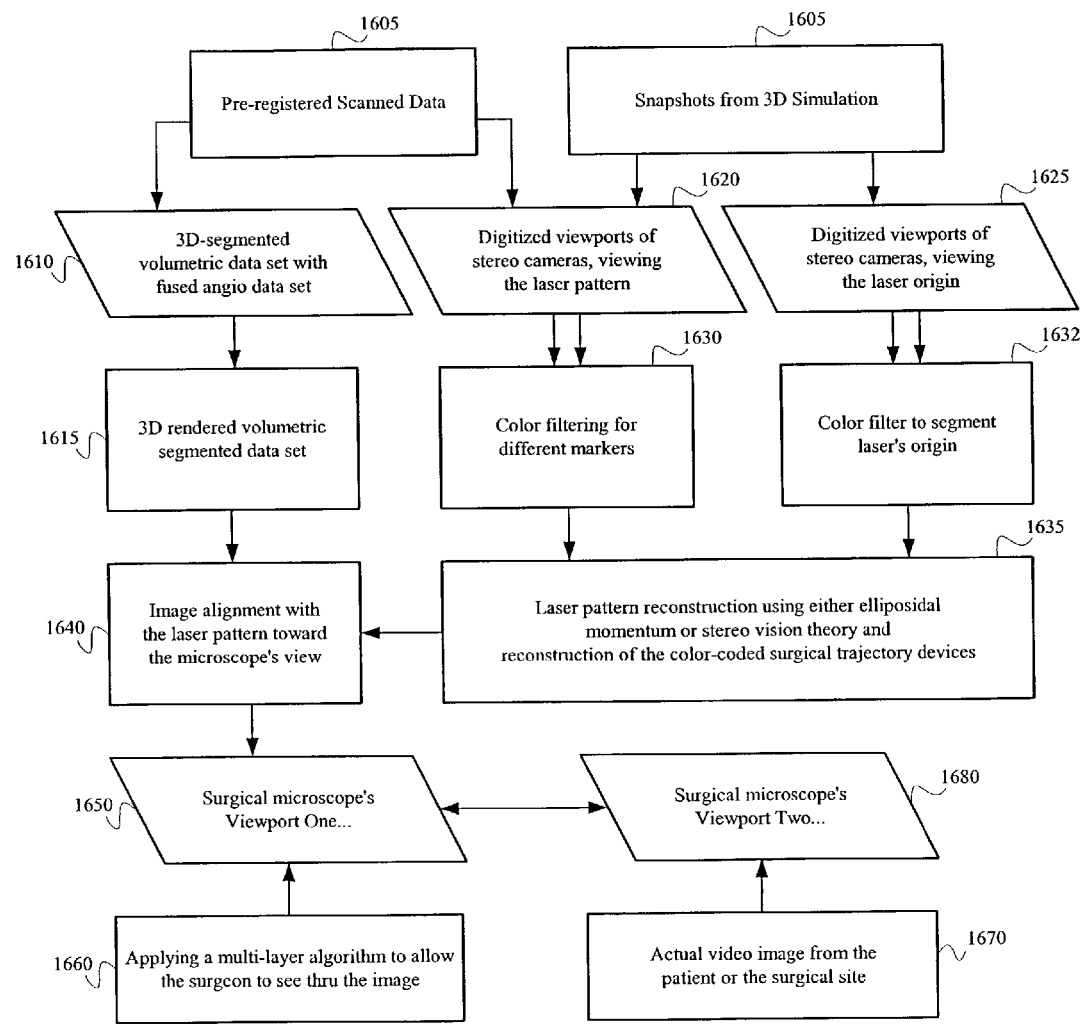
FIG. 16 is a schematic flow chart of one embodiment of a method for visually augmenting stereotactic surgery.

FIG. 16 is a flow chart of an embodiment of a method for dynamic visualization of augmented stereotactic surgery. Such a method can be used in stereotactic surgeries such as stereotactic biopsies or other stereotactic procedures. To accomplish this visualization, two dimensional spatially aligned images from MRI, MR Angiography, or like imagery are stacked on top of each other to produce a volumetric data set. All the simulated pre-registered data (at 1605) is produced from surface extracted images from this data-set and is segmented (at 1610) as described herein. The segmented data set can be color-coded and loaded into a visualization package rendering them volumetric (at 1615) and capable of representing the desired anatomical structures.

Two dimensional digitized cameras display (at 1620) the 3D deformation of the laser pattern on the surface of the patient's anatomy and color-coded medical instruments from different perspectives. These simulated images illustrate the vergence of cameras which are tilted approximately 45 degrees and are approximately two meters away from the surgical site. These camera simulations are typically built around a true-perspective, pinhole camera model which defines the resolution of the images, the simulated camera focal length, and imaging pixel size. Lens distortion is typically ignored. From these 2D camera displays, the laser pattern, patient anatomy and volumetric pre-registered imaging can be constructed.

The projection of the laser field of view is seen as a "see thru" image in the volume set with volumetric-conic sections that can be isolated from the actual image of the microscope. The 2D projection of these multimodalities are then transferred to the surgical microscope. Transferring these images back to the surgical microscope produces a 3D-navigation system for the surgeon to explore alternate possibilities during the surgical procedure.

The realistic simulation of the cameras' field of view is made possible by using a combination of perspective-view characteristics and geometrical transformations. Lens characteristics can be defined by the cameras' viewing angle and its distance from the object. Basic lens relationships for a pinhole camera are:

$$1/u + 1/v = 1/f$$

$$M = V/u$$

$$M = hI/hO$$

where u is the object distance (lens to object)

V is the image distance (lens to image) f is the focal length of the lens

M is the magnification of the image hO is the height of the object hI is the height of the image In one case, the object's distance (u) is known. Given a standard NTSC video camera, the film resolution is 640×480 and the diagonal resolution of our film is the same as image size (hI=800). The object size (hO) is also known. Combining the above equations will give:

$$1/u + hO/u.hI = 1/f$$

In simulating the surgical microscope's view, the magnification (M) is known and can be implemented into the above equations directly, thus yielding:

$$1/u + 1/u.M = 1/f$$

which gives focal length (f) in terms of (u) and (M). Once the focal length is calculated, the lens's viewing angle can be calculated by using the following equation:

$$viewing\_angle = 2.0*57.29*a\tan(21.5/focal\_length)$$

With the viewing angle determined, the lens's captured perspective can be simulated using perspective-window characteristics in a graphics library. Using standard transformation matrixes, an object can then be moved away from the lens in any desired orientation.

In one embodiment two camera pairs with focal lengths of 150 and 100 mms respectively are located approximately two meters away from the patient. These cameras are tilted approximately 45 degrees toward the surgical site to provide adequate information for the 3D reconstruction of the coded objects. Furthermore, the surgical microscope's view for each eye has a six degree vergence angle creating a stereo-view. The magnification and orientation of these stereo-views can be interactively altered to simulate the surgeon's view through the microscope.

Even though the laser is projecting a perfect circle onto the site of operation, the pattern picked up by each camera is not a circle, but an irregular ellipse. This is due to each camera's angle of attack and the curvature of the patient's head. Using color filtering to detect the laser and different markings on the surgical instruments (at 1630), the laser pattern is reconstructed by observing different perspectives of the laser pattern using either ellipsoidal momentum theory or stereo vision theory (at 1635). This is accomplished using color-sensitive filter software. Since the simulated video images and the 3D image are registered, the properties of the 3D image can be added to wherever the laser patterns are located, thus reconstructing the laser patterns as 2D-depth-sensitive, Z-buffers as is well understood in the art.

The reconstruction of the laser pattern projection in 3D can be accomplished using the geometric relationship of the laser and cameras. One such technique is the second-order ellipsoidal momentum. This method requires only one camera field of view and is independent of the laser's source coordinates. To make sense of this method, one can think of the laser pattern as a transparent cone, originating from the tip of the surgical microscope. The base of the cone intersects the surface of the head. The images picked up by a camera are the 2D projections of such an intersection given that the conic sections look like circles when it is viewed from the tip of the cone's axis. Even though the surface of the intersection is non-uniform in this case, the same methodology can be used to determine that the correct viewing angle is obtained when the laser projection is closest to a circle. To calculate the microscope's trajectory, a 2D viewing projection of the laser pattern (from the 3D image) goes through ellipsoidal analysis that is known to persons of ordinary skill in the art. Using second-order ellipsoidal momentum, it is possible to calculate the angle of the microscope's trajectory. The first-order ellipsoidal momentum will reveal the coordinates for the center of the mass on the pattern, while the second-order moment reveals the axial ratio and the angle of rotation. The 3D laser pattern goes through a series of rotations in 3D space and, for each rotation, its axial ratio is calculated. The transformations continue until an axial ratio closest to one is reached (almost a circle). This angle of rotation is the angle of attachment of the microscope, which would be normal to the viewing projection.

Assume that the calculated trajectory angles are $(\theta_x, \theta_y, \theta_z)$. When the 3D data set are rotated in reverse $(-\theta_x, -\theta_y, -\theta_z)$, the viewing projection will be the same as the microscope's field of view. Thus, multiplying the viewing projection matrix by the inverse matrix of the actual transformation matrix, the desired viewing angle can be obtained. Using a seed-fill algorithm, the 3D laser contour can be filled with the data obtained from the registered 3D image. The seed for this fill algorithm is the centroid coordinates of the laser pattern, which are obtained from the first-order ellipsoidal moments. The filled contour is actually a surface patch from the 3D image representing the skin. This patch resembles the view of the surface that the surgeon sees through the microscope. Thus, using ellipsoidal momentum theory and the laser targeting system mentioned previously, reconstructing the surgical microscope's field of view from the laser pattern on the patient's head is possible.

Once the laser pattern from the surface of the head is detected by a camera, the digitized image is sent to the computer for analysis. By using color-sensitive filters, as indicated, the laser pattern can be segmented from the rest of the image. Since the camera views and the 3D data set are registered with each other, the 3D coordinates of the laser pattern can be obtained from the volumetric data by extracting the depth of 2D laser pattern pixels from the adjacent 3D data set pixels.

The ellipsoidal momentum method, however, is unable to predict the path of insertion of a surgical device into the portion of the patient's anatomy of interest. In order to do this, the ellipsoidal method must be used in conjunction with a second method, the stereo vision approach. This approach requires at least four cameras. In the stereo vision method two cameras are used to reconstruct the laser pattern and the spatial coordinates of the surgical trajectory devices. The other pair of cameras calculate the coordinates of the laser source in space. The basic principle involved is triangulation. In this technique, the object must be established between features from two images that correspond to some physical feature in space. Then, provided that the positions of centers of projection, the effective focal length, the orientation of the optical axis, and the sampling interval of each camera, are all known, the depth can be reconstructed using triangulation, a technique that is known to persons of ordinary skill in the medical imaging arts.

Using this technique, each lens of each camera can be modeled as a pinhole assuming that with the first order, all lines of sight intersect at a unique lens center. The distance between the lens's center is specified as "b", and the focal length as "f". The frames "M" and "R" are associated with the simulated left and right camera frames with the origins at the lens centers, and Z axes and occurring along the optical axes, pointing toward the scene in a positive scale. There is also a defined reference frame "W" with the origin at the midpoint of the baseline (Z-axis normal to the baseline, and X-axis pointing along the baseline). The goal of this reconstruction algorithm is therefore to identify the spatial position of the point "P" in reference to the frame "W" as P=(Xw, Yw, Zw). The input to this algorithm is the 2D projection of the point "P" to the "L & R" frames as $(x_L, y_L)$ and $(x_R, y_R)$. The primary goal is to determine the depth (Zw) as close as possible to its actual value in space.

In one embodiment the right camera can be rotated about the right lens center by $\theta$, and the left camera can be rotated about the left lens center by $-\theta$. An analytical relationship between range, disparity and vergence angle is well known in the art. This provides the coordinates of the point P=(XwYwZw). Expressed in the left and right camera coordinate system respectively:

$$\begin{bmatrix} X_L \\ Y_L \\ Z_L \end{bmatrix} = \begin{matrix} \left(X_w + \frac{b}{2}\right) \cdot \cos\theta - (Z_w \cdot \sin\theta) \\ Y_w \\ \left(X_w + \frac{b}{2}\right) \cdot \sin\theta - (Z_w \cdot \cos\theta) \end{matrix}$$

-continued $$\begin{bmatrix} X_R \\ Y_R \\ Z_R \end{bmatrix} = \begin{pmatrix} \left(X_w + \frac{b}{2}\right) \cdot \cos\theta - (Z_w \cdot \sin\theta) \\ Y_w \\ \left(X_w + \frac{b}{2}\right) \cdot \sin\theta - (Z_w \cdot \cos\theta) \end{pmatrix}$$

Perspective transformation yields the following image coordinates:

$$x_L = f \cdot \frac{\left(X_w + \frac{b}{2}\right) \cdot \cos\theta - (Z_w \cdot \sin\theta)}{\left(X_w + \frac{b}{2}\right) \cdot \sin\theta - (Z_w \cdot \cos\theta)}$$

$$x_R = f \cdot \frac{\left(X_w + \frac{b}{2}\right) \cdot \cos\theta - (Z_w \cdot \sin\theta)}{-\left(X_w + \frac{b}{2}\right) \cdot \sin\theta - (Z_w \cdot \cos\theta)}$$

Solving both equations for $X_w$ and equating them, thus eliminates $X_w$. Solving for $Z_w$:

$$Z_w = \frac{b}{\frac{f\sin\theta - x_R\cos\theta + f\sin\theta x_L \cos\theta}{f\cos\theta - x_R\sin\theta + f\sin\theta x_L\cos\theta}}$$

$$Z_w = \frac{b(f\cos\theta - x_L\sin\theta)(f\cos\theta + x_R\sin\theta)}{f(x_L - x_R)\cos 2\theta + (f^2 + x_L x_R)\sin\theta}$$

Using this algorithm, the 3D coordinates of the color-coded surgical trajectory device, the projected laser pattern on the patient's head, and the origin of the laser, can be calculated. Using this data, the trajectory angles $(\theta_x, \theta_y, \theta_z)$ for the surgical device and the laser pattern can then be calculated. As mentioned for the ellipsoidal momentum theory, if the 3D data set is rotated in reverse $(-\theta_x, -\theta_y, -\theta_z)$ the viewing projection will be the same as the microscope's field of view. Thus, multiplying the viewing projection matrix by the inverse matrix of the actual transformation matrix, the desired viewing angle can be obtained. This angle resembles the view of the surface that the surgeon views through the surgical microscope.

As described herein, the 3D volumetric data can be oriented to be in alignment with the laser pattern's projection axis. The orientation of the laser's projection axis can be calculated from the two known points on the cone's major axis. From this information, the volumetric conic section between the laser pattern and the 3D image can be obtained. By moving a vector along the surface of the cone, it is possible to calculate all of the intersecting points between the cone and our volumetric data set. The parametric equation of a cone includes:

$X = 1 \cdot \tan\theta \cos\alpha + x_1$ $Y = 1 + y_1$ $Z = 1 \cdot \tan\theta \sin\alpha + z_1$ where $R = 1 \cdot \tan\theta$, $(x_1, y_1, z_1)$ are the coordinates of the origin of the cone and $\theta$ is the angle between the cone's axis and sen-1i-axis (FIG. 4.9).

This formula represents a cone with its major axis along the y axis. To transfer this cone to the image's virtual space coordinates, we must multiply (X,Y,Z) to an orientation matrix. This orientation matrix is the inverse of the orientation matrix obtained from the transformations of the actual image with respect to the cone. If we increment $\alpha$ and l, the surface of the cone will be covered, as will all of the intersection points between the cone and the image. Once the contours of the cone are defined, one can calculate all the voxels within the conic section by using seed-fill algorithms. Using cut-plain techniques described herein, it is possible to make cuts, orthogonal to the cone's major axis, one layer at a time. These multi-modualities can be observed as "Raw" monochromic images orthogonal to the tip of the trajectory device as it moves through the object. The rendering, after this alignment, is followed by reformatting one data set along the common coordinate system to achieve an image overlay. Different encoding into color spaces, and algebraic combination into a single image, allows for an efficient multimodality display.

Once reconstructed, the laser pattern outline of the microscopes' field of view is aligned with the 3D rendered volumetric segmented data (at 1640). This projection is presented to the surgeon via one of the microscope's eyepieces (at 1650). To enhance the impact of the 3D rendered volumetric segmented data, the images are transparent (at 1660) allowing a surgeon to see through the image and view the actual patient anatomy. The surgeon is also presented actual video of the patent's anatomy from the surgical site (at 1670) via a second eyepiece of the microscope (at 1680). Viewing both presentations, the surgeon can fuse the image creating an augmented presentation of the surgical site.

Having such a view allows a surgeon to plan obstacle avoidance involved in neurosurgery and other precision oriented surgical procedures. This type of planning requires the representation of space occupancy. Assuming that all of the critical organs are now interactively or automatically delineated from imaging modalities, different trajectories relating to possible entry points, and the target, can be generated and the most appropriate trajectory selected. For the surgeon to interactively investigate the possible surgical trajectories, a pointing device is used as optimized by the cameras.

Adding color codes to this pointing device allows the computer to distinguish this instrument from the rest of the image. Once the color codes are optimized by passing the video images through the color-sensitive filter, the orientation of the device in 3D space can be calculated. Since the relative spatial coordinates of the cameras are known, the 3D spatial coordinates of the markers can be calculated by using trigonometric equations. At this point, by using the methods described previously, the addition of the 3D spatial coordinates of the pointer to the registered image allows the surgeon to visualize its trajectory into the 3D image. These trajectories can be displayed on the external monitors, allowing the surgeon to visualize all possible paths from the surface to the lesion as multimodalities.

It is apparent from the foregoing description that this invention provides improved means for navigating through the anatomy during actual surgical procedures. The system enables the surgeon to select and adjust the display with the same tool that is being utilized to perform the procedure, without requiring extra manual operations. Since the displays are provided immediately in real time, the imaging does not require any interruption of the procedure. In addition, the virtual images provided by this system are continuously correlated with the images that are obtained through conventional means.

It will be further appreciated by persons of ordinary skill in the art that the invention is not limited in its application to neurosurgery, or any other kind of surgery or medical diagnostic applications. For example, systems implementing the invention can be implemented for actual nautical or aviation navigation utilizing information from satellites to obtain the "pre-op" scan data. The pointing device can be implemented by the vessel or aircraft itself, and the video display could be replaced by special imaging goggles or helmets.

The foregoing description of the preferred embodiments of the invention has been presented solely for purposes of illustration and description, and is not exhaustive or limited to the precise forms disclosed. Many modifications and variations are possible in light of the above teaching. The spirit and scope of the invention are to be defined by reference to the following claims, along with their full scope of equivalents.

What is claimed is:

1. A system for augmented viewing of a patient target site in a surgical setting by a user, comprising:
    a computer for storing scan data of the patient target region, and for constructing from the stored data, a three dimensional perspective volumetric image of the target site as seen from a selected orientation;
    a viewing device, the device having a first ocular instrument and a second ocular instrument in which the patient target site can be viewed, and in which the three dimensional perspective volumetric image can be projected, forming a fused image using the patient target site view and the three dimensional perspective volumetric image;
    a tracking device coupled to the computer for tracking the selected orientation of the viewing device; and
    a calibration module in the computer for placing the viewing device in the same coordinate system as the patient in response to tracking information received from the tracking device, wherein the selected orientation from which the volumetric image of the target is constructed by the computer is the selected orientation of the second ocular instrument.

2. The system of claim 1 wherein the patient target site can be viewed in the first ocular instrument and the three dimensional perspective volumetric image can be projected in the second ocular instrument.

3. The system of claim 1 wherein the patient target site can be viewed in the first and second ocular instrument and the three dimensional perspective volumetric image can be projected in the second ocular instrument.

4. The system of claim 1 wherein the patent target site can be viewed in the first and second ocular instrument and the three dimensional perspective volumetric image can be projected in the first and second ocular instrument.

5. The system of claim 1 wherein scan data is selected from a group comprising computed tomography, magnetic resonance imaging data, single photon emission computed tomography, x-ray data, positron emission data, ultrasound data, video data, and computed axial tomography data.

6. The system of claim 1 wherein an orientation of a surgical tool is projected on the three dimensional perspective volumetric image of the target site.

7. The system of claim 1 wherein a position of a surgical tool is projected on the three dimensional perspective volumetric image of the target site.

8. The system of claim 1 further comprising a laser scanner mounted on the viewing device for scanning a laser beam over a surface of the patient target region to create a laser pattern on the patient, and wherein the tracking device included two or more cameras for viewing the laser pattern on the patient from two or more different orientations.

9. The system of claim 8 wherein the calibration module is operative to match surface features of the patient, as determined from the volumetric scan data of the patient, with corresponding surface features, as determined from the laser pattern on the patient, to place the scan data in the same frame of reference as the patient.

10. The system in claim 8 wherein the calibration module is operative to determine, from the laser pattern on the patient as viewed by the two or more cameras, the selected orientation of the second ocular instrument.

11. The system of claim 8 wherein the two or more cameras includes a first pair of cameras to observe the patient surface image and a second pair of cameras to track a source of the laser beam.

12. The system of claim 1, further comprising a tracked surgical insertion device having an orientation and a position, the surgical insertion device projected on the three dimensional perspective volumetric image of the target site.

13. A method for augmented viewing of a patient target site in a surgical setting through a viewing device having a pair of ocular instruments, the method comprising:
    storing scan data of the patient target region in a computer, the scanned data having a scanned data coordinate system;
    tracking the position of the patient and the position and orientation of the viewing device;
    registering a patient coordinate system with the scanned data coordinate system;
    constructing a three dimensional perspective volumetric image of the target site using the stored scanned data with a computer processor to create said three dimensional perspective volumetric image from the position and orientation of the viewing device; and injecting the three dimensional perspective volumetric image in the viewing device such that a user sees both an actual image of the patient and the constructed three dimensional perspective volumetric image in the combined ocular instrument.

14. The method of claim 13 further comprising mounting a laser scanner on the viewing device for scanning a laser beam over a surface of the patient target region to create a laser pattern on the patient.

15. The method of claim 14 further comprising matching surface features of the patient, as determined from the volumetric scan data of the patient, with corresponding surface features, as determined from the laser pattern on the patient, to place the scanned data in the patient coordinate system.

16. The method of claim 13 further comprising identifying a field of view and orientation of the viewing device.

17. The method of claim 13 wherein scan data is selected from a group comprising computed tomography, magnetic resonance imaging data, single photon emission computed tomography, x-ray data, positron emission data, ultrasound data, video data, and computed axial tomography data.

18. A system for augmented stereotactic surgery, comprising:
    a set of scanned image data;
    a microscope having a microscopic field of view, the microscope having a first and a second ocular instrument;
    a laser scanning device aligned to project an outline of the microscopic field of view on a patient anatomy;
    a computer having a construction module and a registration module, the construction module configured for constructing a three dimensional perspective volumetric representation of the set of scanned image data, wherein the registration module is configured for aligning the outline of the microscopic field of view with the three dimensional perspective volumetric representation of the set of scanned image data; and a image injection device coupled to the microscope for injecting the three dimensional perspective volumetric representation of the set of scanned image data in the microscopic field of view.

19. The system of claim 18 wherein the intraoperative imagery of the microscopic field of view can be viewed in the first ocular instrument and the three dimensional perspective volumetric representation of the set of scanned data can be injected in the second ocular instrument.

20. The system of claim 18 wherein the intraoperative imagery of the microscopic field of view can be viewed in the first and second ocular instrument and the three dimensional perspective volumetric representation of the set of scanned data can be injected in the second ocular instrument.

21. The system of claim 18 wherein the intraoperative imagery of the microscopic field of view can be viewed in the first and second ocular instrument and the three dimensional perspective volumetric representation of the set of scanned data can be injected in the first and second ocular instrument.

22. The system of claim 18 wherein an orientation of a surgical tool is projected on the three dimensional perspective volumetric representation of the set of scanned data.

23. The system of claim 18 wherein a position of a surgical tool is projected on the three dimensional perspective volumetric representation of the set of scanned data.

24. The system of claim 18 further comprising a tracking device having two or more cameras for viewing the outline of the microscopic field of view from two or more different orientations wherein the two or more cameras includes a first pair of cameras to observe a patient surface image and a second pair of cameras to track a source of a laser beam originating from the laser scanning device.

25. An apparatus for combining a representation of a patient anatomy generated from preexisting image data with dynamic imagery, comprising:

a surgical instrument having an optical field of view for dynamic viewing of the patient anatomy;

a laser scanning device coupled to the surgical instrument and configured to project the surgical instrument's optical field of view on the patient anatomy;

a computer capable of creating a three dimensional perspective volumetric image of the preexisting image data in registration with the optical field of view of the surgical device and the patient anatomy based on the surgical instrument's orientation and optical field of view; and a combining device to inject the three dimensional perspective volumetric image of the preexisting image data in the optical field of view of the surgical instrument.

* * * * *